US010555947B2

(12) United States Patent
Musunuri et al.

(10) Patent No.: US 10,555,947 B2
(45) Date of Patent: *Feb. 11, 2020

(54) OPHTHALMIC COMPOSITIONS AND METHODS OF USE

(71) Applicant: Ocugen, Inc., Malvern, PA (US)

(72) Inventors: Shankar Musunuri, Chester Springs, PA (US); Sandeep Jain, Oak Park, IL (US); Rasappa Arumugham, Lansdale, PA (US); Arun K. Upadhyay, West Chester, PA (US); Matthew Nudell, Lafayette, CO (US); Gopalam Somasekhar, Collegeville, PA (US)

(73) Assignee: OCUGEN, INC., Malvern, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/946,709

(22) Filed: Apr. 5, 2018

(65) Prior Publication Data
US 2018/0333414 A1 Nov. 22, 2018

Related U.S. Application Data

(60) Provisional application No. 62/509,015, filed on May 19, 2017, provisional application No. 62/591,548, filed on Nov. 28, 2017.

(51) Int. Cl.
| | | |
|---|---|---|
| *A61K 31/517* | (2006.01) |
| *A61K 9/107* | (2006.01) |
| *A61K 9/00* | (2006.01) |
| *A61P 27/04* | (2006.01) |
| *A61K 47/10* | (2017.01) |
| *A61K 45/06* | (2006.01) |
| *A61K 47/26* | (2006.01) |
| *A61K 9/10* | (2006.01) |
| *A61K 9/06* | (2006.01) |
| A61K 31/573 | (2006.01) |
| A61K 31/155 | (2006.01) |
| A61K 31/4725 | (2006.01) |

(52) U.S. Cl.
CPC .......... *A61K 31/517* (2013.01); *A61K 9/0048* (2013.01); *A61K 9/06* (2013.01); *A61K 9/10* (2013.01); *A61K 9/1075* (2013.01); *A61K 45/06* (2013.01); *A61K 47/10* (2013.01); *A61K 47/26* (2013.01); *A61P 27/04* (2018.01); *A61K 31/155* (2013.01); *A61K 31/4725* (2013.01); *A61K 31/573* (2013.01); *A61K 2300/00* (2013.01)

(58) Field of Classification Search
None
See application file for complete search history.

(56) References Cited

U.S. PATENT DOCUMENTS

| | | |
|---|---|---|
| 8,575,207 B2 | 11/2013 | Gil et al. |
| 9,597,328 B2 | 3/2017 | Jain et al. |
| 2005/0182039 A1* | 8/2005 | Meyering ............ A61K 9/0048 514/178 |
| 2005/0196370 A1 | 9/2005 | Yu et al. |
| 2008/0050335 A1 | 2/2008 | Faour et al. |
| 2012/0003296 A1 | 1/2012 | Shantha et al. |
| 2012/0076738 A1 | 3/2012 | Graeber et al. |
| 2012/0093876 A1 | 4/2012 | Ousler, III et al. |
| 2014/0088199 A1 | 3/2014 | Sharma |
| 2016/0243116 A1* | 8/2016 | Jain ...................... A61K 31/498 |

FOREIGN PATENT DOCUMENTS

| | | |
|---|---|---|
| WO | WO2006/004577 A2 | 1/2006 |
| WO | WO2013/124415 A1 | 8/2013 |

OTHER PUBLICATIONS

Janse van Rensburg et. al. in CME Apr. 31, 2013 (4) (Year: 2013).*
Chime et al. In Nanoemulsions—Advances in Formulation, Characterization and Applications in Drug Delivery (Chapter 3), pp. 77-126 in Application of Nanotechnology in Drug Delivery (2014) (Year: 2014).*
Perry et al. in Archives of Ophthalmology;126(8):1046-1050 (2008) (Year: 2008).*

(Continued)

*Primary Examiner* — Dennis Heyer
(74) *Attorney, Agent, or Firm* — Don D. Cha; HDC IP Law, LLP

(57) ABSTRACT

The present invention provides a composition comprising two or more of the following pharmaceutically active compounds: (i) an alpha 2 adrenergic agonist; (ii) a corticosteroid; (iii) a lymphocyte function-associated antigen antagonist; (iv) a non-steroidal anti-inflammatory drug (NSAID); (v) a sodium channel blocker; and (vi) an antibiotic, provided at least one of the pharmaceutically active compound is selected from the group consisting of (i) alpha 2 adrenergic agonist and (ii) corticosteroid. The present invention also provides a method for using such composition to treat an eye disorder such as a dry eye syndrome; ocular graft-versus-host-disease; ocular rosacea; allergic conjunctivitis; autoimmune ocular surface disease; thygeson's superficial punctuate keratopathy; herpes zoster keratitis; Stevens-Johnson syndrome; keratitis; conjunctivitis; blepharitis; blepharochalasis; conjunctivochalasis; blepharoconjunctivitis; blepharokeratoconjunctivitis; post-operative inflammation or pain from ocular surgery; scleritis; episcleritis; anterior uveitis; iritis; cyclitis; ocular surface vascular disorder; ulcerative keratitis; photokeratitis; dacryocystitis; eyelid disorder; congenital alacrima; xerophthalmia; dacryoadenitis; vernal keratoconjunctivitis; pinguecula; and/or ocular surface disorder induced by chemical burns, thermal burns, or physical insult to the ocular surface.

15 Claims, 2 Drawing Sheets

(56) References Cited

OTHER PUBLICATIONS

Restasis in https://www.drugs.com/pro/restasis.html (retrieved from the internet Aug. 23, 2019) (Year: 2019).*
Office Action dated Sep. 26, 2016 for U.S. Appl. No. 15/051,654.
Cantor, "Brimonidine in the treatment of glaucoma and ocular hypertension," Therap. Clin. Risk Management, 2006, 2(4), 337-346.
Fairbanks et al., "Pharmacological Profiles of Alpha 2 Adrenergic Receptor Agonists Identified Using Genetically Altered Mice and Isobolographic Analysis," Pharmacol. Ther. Aug. 2009, 123(2), 224-238.
Gil et al., "alpha-1-Adrenergic Receptor Agonist Activity of Clinical alpha-Adrenergic Receptor Agonists Interferes with alpha-2-Mediated Analgesia," Anesthesiology, 2009, 110, 401-407.
Wikberg-Matsson et al., "Potent a2A-Adrenoceptor—Mediated Vasoconstriction by Brimonidine in Porcine Ciliary Arteries," IOVS, Aug. 2001, vol. 42, No. 9, pp. 2049-2055.
Stone et al., "The a2a Adrenergic Receptor Subtype Mediates Spinal Analgesia Evoked by a2 Agonists and Is Necessary for Spinal Adrenergic—Opioid Synergy," J. Neurosci., 1997, 17(18), pp. 7157-7165.
Office Action dated Jul. 26, 2018 for U.S. Appl. No. 15/883,361.
Office Action dated Feb. 7, 2019 for U.S. Appl. No. 15/883,361.
Office Action dated Mar. 7, 2019 for U.S. Appl. No. 15/944,332.
Office Action dated Oct. 10, 2019 for U.S. Appl. No. 15/944,332.
Wiltz "Hyaluronic Acid and Its Skin Absorption," Jul. 18, 2017, https://healthfully.com/292302-hyaluronic-acid-and-its-skin-absorption.html.

* cited by examiner

OPHTHALMIC COMPOSITIONS AND METHODS OF USE

CROSS-REFERENCE TO RELATED APPLICATIONS

This application claims the priority benefit of U.S. Provisional Application Nos. 62/509,015, filed May 19, 2017, and 62/591,548, filed Nov. 28, 2017, which are incorporated herein by reference in their entirety.

FIELD OF THE INVENTION

The present invention relates to a composition comprising first therapeutically active compound selected from the group consisting of an alpha 2 adrenergic agonist and a corticosteroid and at least one second therapeutically active compound, wherein the second therapeutically active compound is different from the first therapeutically active compound. In some embodiments, the second therapeutically active compound is selected from the group consisting of an alpha 2 adrenergic agonist, a corticosteroid, a lymphocyte function-associated antigen antagonist, a non-steroidal anti-inflammatory drug, a sodium channel blocker (i.e., "ENaC inhibitor" or "ENaC blocker"), an antibiotic and a combination of two or more thereof. The present invention also provides a method for treating various clinical conditions associated with an eye using the composition of the invention.

BACKGROUND OF THE INVENTION

Dry eye disease (DED) is a common ocular disorder involving the aberrant production and stability of tear film, which results in damage to the ocular surface and is correlated with symptoms of ocular discomfort. DED is also recognized as keratoconjunctivitis sicca (KCS), sicca syndrome, keratitis sicca, xerophthalmia, dry eye syndrome (DES), dysfunctional tear syndrome (DTS), ocular surface disease (OSD) or dry eye. DED is caused by chronic instability of preocular tear film. Tear film instability can be triggered by insufficient tear production, or by poor tear film quality that results in increased tear evaporation. Furthermore, dry eye is typically categorized into two groups: (i) aqueous tear deficient dry eye disease; and (ii) evaporative dry eye disease.

DED is a result of changes to the lacrimal functional unit (LFU). The LFU is composed of the lacrimal glands, cornea, eyelids, meibomian glands, conjunctiva, goblet cells, and ocular nerves. The LFU is responsible for the sustained production of adequate tear film to consistently lubricate the ocular surface. Structural changes to the LFU can induce tear film instability and insufficiency, which in turn can lead to tear hyperosmolarity. Chronic osmotic stress from tear film can activate stress associated pathways in ocular surface epithelial cells, thereby triggering a pro-inflammatory response that involves a mix of chemokines, cytokines, and matrix metalloproteinases. The subsequent maturation of antigen-presenting cells (APC's) on the ocular surface leads to the migration, activation, and expansion of autoreactive T cell lymphocytes as well as other leukocytic classes in the LFU. The constant recruitment of pro-inflammatory leukocytes onto the ocular surface inflicts epithelium damage in the form of small abrasions and epithelium barrier defects. These abrasions can eventually progress to superficial punctuate keratitis, squamous metaplasia, extracellular matrix deposits, decreased goblet cell differentiation, increased epithelial cell turnover (epitheliopathy), and significant ocular surface nerve damage and neuropathy.

As DED progresses, lacrimal gland obstruction, meibomian gland orifice obstruction, thickened eyelid margins, cloudy, solid, or granular meibum secretion, eyelid telangiectasia, and meibomian gland dysfunction become common clinical features. In advanced cases, dry eye can cause fibrotic thickening of the cornea and conjunctiva, filamentous keratitis, mucoid clumping, trichiasis, symblepharon, keratinization of the eyelids and meibomian glands, corneal and conjunctival erosion and thinning, corneal and conjunctival neovascularization, corneal and conjunctival scarring, corneal ulceration, and corneal perforation. Most importantly, prolonged ocular surface inflammation can lead to moderate or absolute loss/atrophy of the meibomian glands, lacrimal glands, and conjunctival goblet cells, and subsequently a dramatic reduction in tear film production and the onset of permanent DED.

DED prevalence increases with age. The most common causes of dry eye are contact lens usage, autoimmune disorders, systemic drug effects, and refractive surgeries, particularly in middle-aged and older adults. DED also occurs in a higher percentage of women than men, especially in women entering menopause or pregnancy; hormone imbalances during menopause or pregnancy can cause lacrimal gland and ocular surface inflammation and tear film abnormalities.

Typically, clinicians prescribe artificial tear eyedrops and topical corticosteroids for short-term relief of DED. Antibiotics (e.g., tetracyclines and macrolides), non-steroidal anti-inflammatory agents, autologous serum drops, omega fatty acids, mucin secretagogues, artificial tears, and anti-inflammatory agents are also used to combat DED symptoms. In addition, prosthetic scleral lenses (i.e., PROSE) that also serve as supplemental tear reservoirs are increasingly being prescribed to enhance ocular surface hydration in patients with chronic DED. Hot eyelid compresses are often utilized to treat meibomian gland dysfunction, a primary driver of evaporative dry eye disease. In advanced cases of DED, punctual plugs can be installed to block tear drainage. In severe cases of dry eye, tarsorrhaphy surgery, tear duct cauterization, or amniotic membrane transplant might be required to reduce tear evaporation.

Currently there are only two pharmaceutical agents that are FDA approved for the treatment of dry eye: cylcosporine A ophthalmic emulsion (Restasis®) and lifitegrast ophthalmic solution (Xiidra™). Restasis® 0.05% is a topical immunomodulator indicated to increase tear production in patients whose tear production is presumed to be suppressed due to ocular inflammation associated with keratoconjunctivitis sicca (Restasis® Prescribing Information). Xiidra™ 5% is a lymphocyte function-associated antigen (LFA-1) antagonist indicated for the treatment of signs and symptoms of dry eye disease (Xiidra™ Prescribing Information). Given the complexity, severity, and frequency of DED, and given the limited modes of action by which these two compounds treat dry eyes, there is a medical need for other dry eye therapies, particularly those with multiple modes of action that target the wider dry eye population and are effective and safe for early relief and long-term daily use as well.

In addition, both Xiidra® and Restasis® have anti-inflammatory properties and reduce cytokine release and T-cell activation. They work by reducing eye inflammation in people who suffer from dry eye syndrome. Unfortunately, there are no consistent and effective formulations that allow the efficient uptake of these active pharmaceutical ingredients for extended period into ocular surface tissues. Thus, these formulations require continual application for effective treatment of dry eye syndrome. While ointment or cream formulations may allow longer residence time, such formulations can cause discomfort and blurry vision.

Accordingly, there is a need for compositions and methods for effective treatment of dry eye syndrome that reduce or prevent the undesired local side effects observed in current formulations.

SUMMARY OF THE INVENTION

The present invention provides an ophthalmic composition comprising two or more of the following pharmaceutically active compounds: (i) an alpha 2 adrenergic agonist, a pharmaceutically acceptable salt thereof or a combination thereof; (ii) a corticosteroid; (iii) a lymphocyte function-associated antigen antagonist; (iv) a non-steroidal anti-inflammatory drug (NSAID); (v) a sodium channel blocker; and (vi) an antibiotic, provided at least one of the pharmaceutically active compound is selected from the group consisting of (i) and (ii).

Some aspects of the invention provide a composition comprising (a) first therapeutically active compound selected from the group consisting of an alpha 2 adrenergic agonist, a pharmaceutically acceptable salt thereof or a combination thereof and a corticosteroid; and (b) a second therapeutically active compound, wherein the second therapeutically active compound is different from the first therapeutically active compound and is selected from the group consisting of (i) an alpha 2 adrenergic agonist, a pharmaceutically acceptable salt thereof or a combination thereof, (ii) a corticosteroid, (iii) a lymphocyte function-associated antigen antagonist, (iv) a non-steroidal anti-inflammatory drug (NSAID), (v) a sodium channel blocker, (vi) an antibiotic, and (vii) a combination of two or more thereof. In some embodiments, compositions of the invention comprise (a) an alpha 2 adrenergic agonist, a pharmaceutically acceptable salt thereof or a combination thereof; and (b) a corticosteroid. Still in another embodiment, the compositions of the invention comprise an alpha 2 adrenergic agonist, a pharmaceutically acceptable salt thereof or a combination thereof and (b) a lymphocyte function-associated antigen antagonist. Yet in another embodiment, the compositions of the invention comprise (a) an alpha 2 adrenergic agonist, a pharmaceutically acceptable salt thereof or a combination thereof; and (b) a sodium channel blocker. In another embodiment, compositions of the invention comprise (a) an alpha 2 adrenergic agonist, a pharmaceutically acceptable salt thereof or a combination thereof; and (b) a non-steroidal anti-inflammatory drug. In yet another embodiment, compositions of the invention comprise (a) an alpha 2 adrenergic agonist, a pharmaceutically acceptable salt thereof or a combination thereof and (b) an antibiotic. Still in some embodiments, compositions of the invention comprise (a) a corticosteroid; and (b) a sodium channel blocker. In yet another embodiment; compositions of the invention comprise (a) a corticosteroid; and (b) a lymphocyte function-associated antigen antagonist. In another embodiment; compositions of the invention comprise (a) a corticosteroid; and (b) an alpha 2 adrenergic agonist. Still in another embodiment; compositions of the invention comprise (a) a corticosteroid; and (b) an antibiotic. In another embodiment, compositions of the invention comprise (a) a corticosteroid and (b) a non-steroidal anti-inflammatory drug.

In one particular embodiment, a corticosteroid comprises loteprednol etabonate.

In another particular embodiment, an alpha 2 adrenergic agonist comprises brimonidine, a pharmaceutically acceptable salt thereof, or a combination thereof.

Still in another embodiment, lymphocyte function-associated antigen antagonist comprises lifitegrast.

Another aspect of the invention provides an aqueous ophthalmic solution comprising the composition of the present invention. As used herein, the terms "ophthalmic solution" and "aqueous solution" include a homogeneous solution or a heterogeneous solution. Heterogeneous solutions include, but are not limited to, dispersions (e.g., oil dispersion in an aqueous solution such as emulsions), suspensions, and a combination thereof including other heterogeneous solutions where there are two or more visibly different substances or phases within the solution. In one particular embodiment, the aqueous ophthalmic solution comprises (a) an α2 adrenergic agonist; (b) a lymphocyte function-associated antigen antagonist, a corticosteroid, a sodium channel blocker, an antibiotic, a non-steroidal anti-inflammatory drug or a combination thereof; (c) an oil-in-water emulsion; and (d) a pharmaceutically acceptable excipient. In some embodiments, the pharmaceutically acceptable excipient comprises: (i) an emulsion stabilizing polymer, (ii) a surfactant, (iii) a tonicity modifier or a stabilizer selected from the group consisting of a polyol, a non-reducing disaccharide and a combination thereof, or (iv) a combination thereof. In another particular embodiment, the aqueous ophthalmic solution comprises (a) a corticosteroid; (b) a lymphocyte function-associated antigen antagonist, a sodium channel blocker, an antibiotic, a non-steroidal anti-inflammatory drug, an alpha 2 adrenergic agonist or a combination thereof (c) an oil-in-water emulsion; and (d) a pharmaceutically acceptable excipient. In some embodiments, the pharmaceutically acceptable excipient comprises: (i) an emulsion stabilizing polymer, (ii) a surfactant, (iii) a tonicity modifier or a stabilizer selected from the group consisting of a polyol, a non-reducing disaccharide and a combination thereof, or (iv) a combination thereof.

Another aspect of the invention provides an aqueous ophthalmic solution containing the composition of the present invention. As stated above, the aqueous ophthalmic solution can be an aqueous homogeneous solution, or heterogeneous solution such as aqueous suspension, aqueous dispersion, or a combination of both. Preferably, the aqueous ophthalmic solution contains (a) a first therapeutically active compound selected from the group consisting of an α2 adrenergic agonist, a pharmaceutically acceptable salt thereof, a corticosteroid, and a combination thereof; (b) a second therapeutically active compound selected from the group consisting of lymphocyte function-associated antigen antagonist, a sodium channel blocker, an antibiotic, a non-steroidal anti-inflammatory drug and a combination thereof; and (c) a pharmaceutically acceptable excipient. In some embodiments, the pharmaceutically acceptable excipient comprises: (i) a water-soluble polymer, (ii) a surfactant, (iii) a tonicity modifier or a stabilizer selected from the group consisting of a polyol, a non-reducing disaccharide and a combination thereof, or (iv) a combination thereof.

Still another aspect of the invention provides a method for treating a clinical condition associated with eye, said method comprising administering to a subject in need of such a treatment a therapeutically effective amount of a composition of the invention. In some embodiments, the clinical condition associated with eye is selected from the group consisting of dry eye syndrome (keratoconjunctivitis sicca), sjogren's syndrome, congenital alacrima, xerophthalmia (dry eye from vitamin A deficiency), keratomalacia, thyroid eye disease, ocular rosacea, eyelid disorders, meibomian gland disease, meibomian gland dysfunction, ectropion, blepharitis, blepharochalasis, sarcoidosis, stye, hordeolum, chalazion, ptosis, pterygium, eyelid edema, eyelid dermatitis, trichiasis, madarosis, dacryoadenitis, stevens-johnson syndrome, ocular graft versus host disease, dacryocystitis, conjunctivitis, keratoconjunctivitis, blepharoconjunctivitis, blepharokeratoconjunctivitis, allergic conjunctivitis, vernal conjunctivitis, conjunctival suffusion, conjunctivochalasis, subconjunctival hemorrhage, pterygium, pinguecula, chemosis, iritis, iridocyclitis, anterior uveitis, glaucoma, red eye, keratitis, scleritis, episcleritis, peripheral ulcerative keratitis, neurotrophic keratitis, neurotrophic eye disease, corneal ulcer, ulcerative keratitis, corneal abrasion, photokeratitis, ultraviolet keratitis, exposure keratitis, superficial punctuate keratitis, thygeson's superficial punctuate keratopathy, herpes zoster keratitis, acne rosacea, corneal neovascularization, corneal dystrophy, epithelial basement membrane dystrophy, fuch's dystrophy, posterior polymorphous corneal dystrophy, macular corneal dystrophy, cyclitis, uveitis, iritis, post-operative inflammation following ocular surgery (i.e. eyelid surgery, cataract surgery, corneal surgery, refractive surgery including photorefractive keratectomy, glaucoma surgery, lacrimal gland surgery, conjunctival surgery, eye muscle surgery), ocular surface conditions caused by chemical burns, thermal burns or physical trauma, ocular conditions caused by the following autoimmune or vascular disorders: rheumatoid arthritis, juvenile rheumatoid arthritis, ankulosing spondylitis, reiter's syndrome, enteropathic arthritis, psoriatic arthritis, discoid and systemic lupus erythematosus, multiple sclerosis, graves' disease, antiphospholipid syndrome, sarcoidosis, wegner's granulomatosis, behcet's syndrome, polyarteritis *nodosa*, takayasu's arteritis, dermatomyositis, psoriasis, relapsing polychondritis, vasculitis, sickle cell-anemia, type II diabetes, diabetic retinopathy, and a combination thereof.

A particularly preferred composition contains an ophthalmically active corticosteroid such as loteprednol and at least one other therapeutically active compound. The one other or second therapeutically active compound can be an alpha 2 adrenergic agonist or a pharmaceutically acceptable salt thereof, a lymphocyte function-associated antigen antagonist, a sodium channel blocker, a non-steroidal anti-inflammatory drug, or an antibiotic. The alpha 2 adrenergic agonist or a pharmaceutically acceptable salt thereof can be an alpha-2A or alpha-2B adrenergic agonist. The composition can be formulated as a heterogeneous aqueous solution (such as a nanoemulsion or a suspension or a combination thereof) or as a homogeneous aqueous solution. The heterogeneous solution can be prepared by using, for example, castor oil, corn oil, olive oil, oleic acid or a combination of these components. The compositions typically contains a pharmaceutically acceptable excipient including an emulsion stabilizing polymer, a water-soluble polymer a surfactant, a tonicity modifier or a stabilizer, polysorbate 80, Pemulen®, a polyol, viscosity modifying agent, or other pharmaceutically acceptable excipients known to one skilled in the art, or any combination of these. In some embodiments, the composition is a combination of loteprednol with at least one of the alpha 2A or 2B adrenergic agonist or a pharmaceutically acceptable salt thereof, lifitegrast and a sodium channel blocker (in a single or separate dosage forms) in a pharmaceutically acceptable excipient. In certain compositions there can be any of the other second therapeutically active compounds such as a non-steroidal anti-inflammatory drug (NSAID); an antibiotic.

The compositions of the invention can also be formulated as an aqueous ophthalmic solution. In some embodiments, composition of the invention contains an ophthalmically active corticosteroid; an α2 adrenergic agonist; a lymphocyte function-associated antigen antagonist; a sodium channel blocker, a non-steroidal anti-inflammatory drug (NSAID), an antibiotic or a combination of these compounds; an oil and a pharmaceutically acceptable excipient. In one particular composition, ophthalmically active corticosteroid is loteprednol. In yet another composition, ophthalmically active alpha 2A agonist is brimonidine. Any of these compositions (formulated as a homogeneous ophthalmic aqueous formulation, a heterogeneous ophthalmic aqueous solution, a hydrogel, or an ophthalmic cream) can contain a pharmaceutically acceptable excipient including an emulsion stabilizing polymer, a water-soluble polymer a surfactant, a tonicity modifier or a stabilizer (e.g., polyol, a non-reducing disaccharide and a combination thereof, or a combination of these. The heterogeneous ophthalmic aqueous solution can be an emulsion, suspension or a combination of an emulsion and suspension. One particular composition of the invention has a corticosteroid containing loteprednol and lifitegrast in a pharmaceutically acceptable excipient. Another preferred composition has a corticosteroid containing loteprednol and a sodium channel blocker. Still another preferred composition has an alpha 2 adrenergic agonist containing brimonidine and a sodium channel blocker. A method for treating an eye disorder by administering to a patient in need of such a treatment a therapeutically effective amount of any of the compositions, preferably in the form of nanoemulsions or aqueous solutions, is also provided. The eye disorder can be a dry eye syndrome. Preferably, the composition is administered topically to an eye of the subject.

One particular aspect of the invention provides a composition comprising two or more of the following pharmaceutically active compounds: (i) an alpha 2 adrenergic agonist; (ii) a corticosteroid; (iii) a lymphocyte function-associated antigen antagonist; (iv) a sodium channel blocker; (v) a non-steroidal anti-inflammatory drug; and (vi) an antibiotic, provided the composition comprises at least one of said alpha 2 adrenergic agonist or said corticosteroid. In one embodiment, said alpha 2 adrenergic agonist comprises brimonidine or a pharmaceutically acceptable salt thereof, or a combination thereof. In another embodiment, said corticosteroid comprises loteprednol etabonate, difluprednate, prednisone acetate, prednisolone sodium phosphate, triamcinolone, fluocinolone; fluorometholone, betamethasone, medrysone or a combination thereof.

One particular aspect of the invention provides an ophthalmic composition comprising: a first ophthalmic compound and a second ophthalmic compound that is different from said first ophthalmic compound, wherein said first ophthalmic compound is selected from the group consisting of an alpha 2 adrenergic agonist and a corticosteroid, and wherein said second ophthalmic compound is selected from the group consisting of: (i) an alpha 2 adrenergic agonist; (ii) a corticosteroid (iii) a lymphocyte function-associated antigen antagonist; (iv) a sodium channel blocker; (v) a non-steroidal anti-inflammatory drug; (vi) an antibiotic; and (vii) a combination of two or more thereof. In some embodiments, said first ophthalmic compound is an alpha 2 adrenergic agonist selected from the group consisting of brimonidine, a pharmaceutically acceptable salt thereof, and a combination thereof. In other embodiments, said first ophthalmic compound is corticosteroid selected from the group consisting of loteprednol etabonate, difluprednate, prednisone acetate, prednisolone sodium phosphate, triamcinolone, fluocinolone; fluorometholone, betamethasone, medrysone or a combination thereof. In one particular embodiment, said first ophthalmic compound is brimonidine, a pharmaceutically acceptable salt thereof, or a combination thereof, and wherein said second ophthalmic compound is loteprednol, a pharmaceutically acceptable salt thereof, or a combination thereof. Still in other embodiments, the composition further comprises a pharmaceutically acceptable excipient. Yet in another particular embodiment, said first ophthalmic compound comprises from about 0.01% to about 0.5% w/w of the total composition. In another particular embodiment, said second ophthalmic compound comprises from about 0.01% to about 0.5 w/w of the total composition. Still in other embodiments, said corticosteroid comprises loteprednol etabonate, difluprednate, prednisone acetate, prednisolone sodium phosphate, triamcinolone, fluocinolone;

fluorometholone, betamethasone, medrysone, or a combination thereof. In yet another embodiment, composition is formulated as a heterogeneous aqueous solution. Still in another embodiment, the heterogeneous aqueous solution comprises an emulsion, a suspension, or a combination thereof. In one particular instance, said emulsion is nanoemulsion. In another embodiment, the heterogeneous aqueous solution comprises an emulsion, a gel, or combination thereof. Still in another embodiment, said composition is formulated as a homogeneous aqueous solution. Yet in another embodiment, said pharmaceutically acceptable excipient comprises an emulsion stabilizing polymer, a water soluble polymer a surfactant, a tonicity modifier, a viscosity modifying agent, a stabilizer, or a combination thereof. In one particular embodiment, said lymphocyte function-associated antigen antagonist comprises N-{[2-(1-Benzofuran-6-ylcarbonyl)-5,7-dichloro-1,2,3,4-tetrahydro-6-isoquinolinyl]carbonyl}-3-(methyl sulfonyl)-L-phenylalanine (i.e., lifitegrast). Still in another embodiment, said sodium channel blocker comprises amiloride, amiloride analogues/derivatives, benzamil, benzamil analogues/derivatives, phenamil, phenamil analogues/derivatives, pyrazinoylguanidine analogues/derivatives.

Another particular aspect of the invention provides a method for treating an eye disorder, said method comprising administering to a subject in need of such a treatment a therapeutically effective amount of any of the compositions disclosed herein. In one particular embodiment, said eye disorder is selected from the group consisting of a dry eye syndrome; ocular graft-versus-host-disease; ocular rosacea; allergic conjunctivitis; autoimmune ocular surface disease; thygeson's superficial punctuate keratopathy; herpes zoster keratitis; Stevens-Johnson syndrome; keratitis; conjunctivitis; blepharitis; blepharochalasis; conjunctivochalasis; blepharoconjunctivitis; blepharokeratoconjunctivitis; postoperative inflammation or pain from ocular surgery; scleritis; episcleritis; anterior uveitis; iritis; cyclitis; ocular surface vascular disorder; ulcerative keratitis; photokeratitis; dacryocystitis; eyelid disorder; congenital alacrima; xerophthalmia; dacryoadenitis; vernal keratoconjunctivitis; pinguecula; and ocular surface disorder induced by chemical burns, thermal burns, or physical insult to the ocular surface. In another embodiment, said dry eye syndrome is selected from the group consisting of sjogren's syndrome, meibomian gland dysfunction and keratoconjunctivitis. Still yet in another embodiment, said eyelid disorder comprises eyelid inflammation, pain and/or edema. In some instances, said composition is administered topically to an eye of said subject.

Surprisingly and unexpectedly, in some embodiments, use of two or more APIs in a single formulation was shown to provide a synergistic effect. Such a synergistic effect allows use of a smaller amount of each API compared to using such an API alone. In other embodiments, use of two or more APIs in a single formulation significantly reduces the side-effects. In some embodiments, the rate of occurrence of side-effect is reduced by a statistically significant amount (e.g., statistical p-value of ≤0.1, typically ≤0.05, and often ≤0.01).

DETAILED DESCRIPTION OF THE INVENTION

Figure 1A:
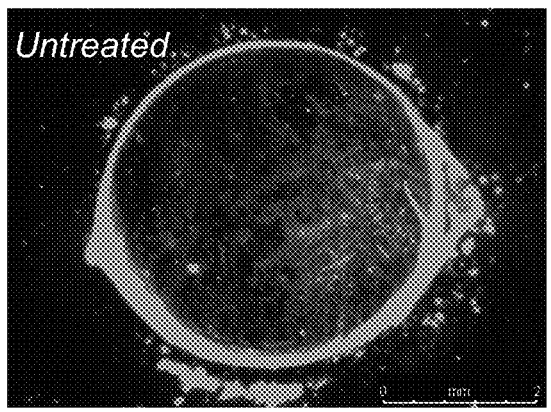
FIG. 1A shows fluorescein staining from the mouse dry-eye disease model treated with placebo, two commercial products (cyclosporine and lifitegrast), and an ophthalmic composition of the present invention.
Figure 1A:
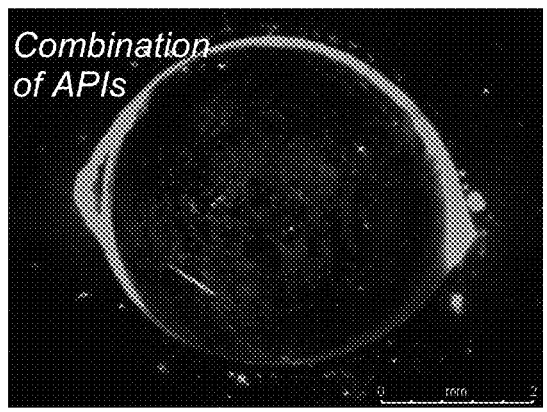
Figure 1A:
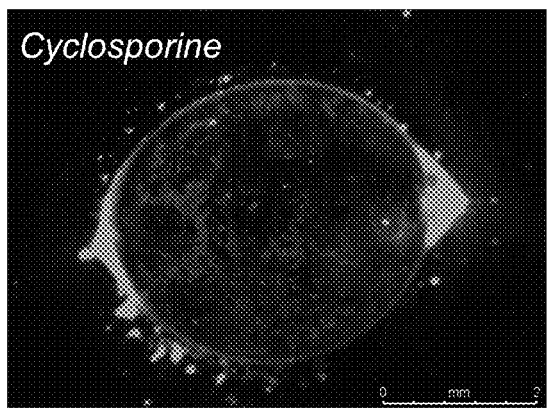
Figure 1A:
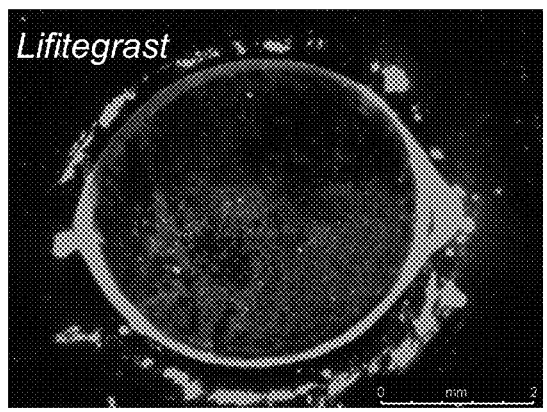
Figure 1B:
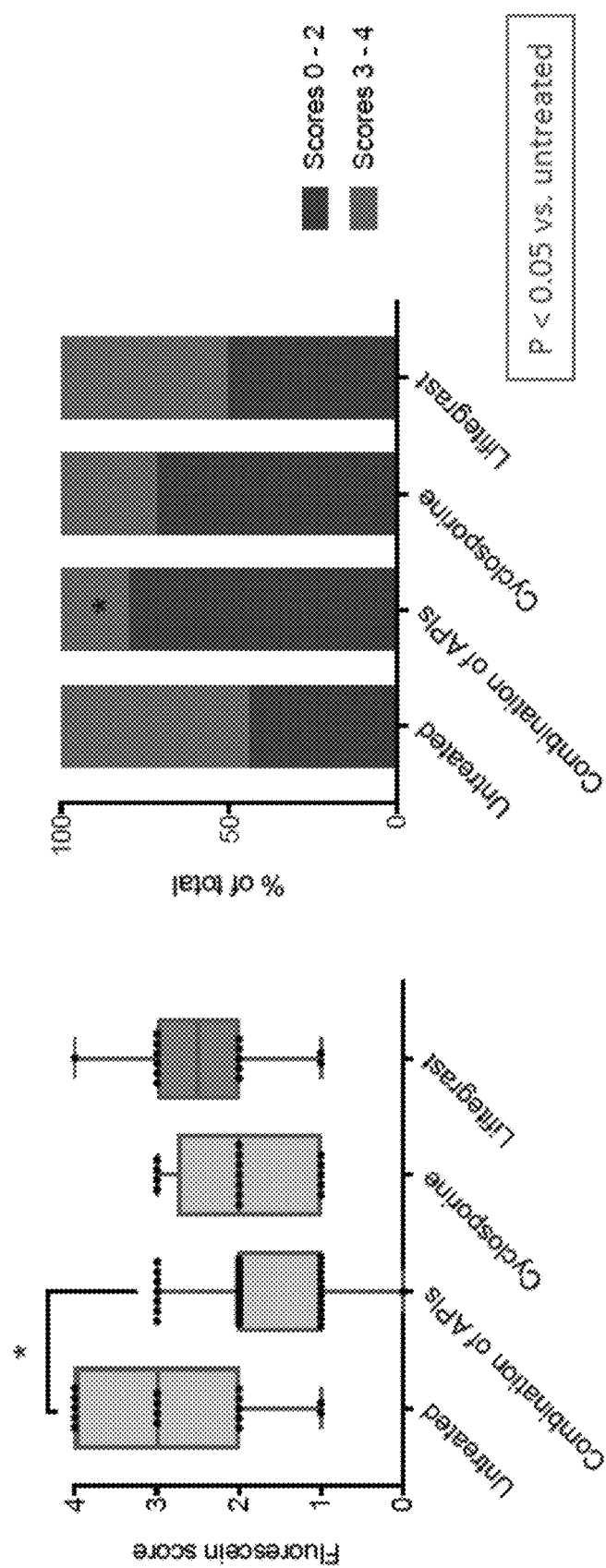
FIG. 1B is a graph showing results of corneal inflammation from the mouse dry-eye disease model treated with placebo, two commercial products (cyclosporine and lifitegrast), and an ophthalmic composition of the present invention.

One aspect of the invention provides a composition comprising (i) a first therapeutically active compound (i.e., a first ophthalmic compound) selected from the group consisting of an alpha 2 adrenergic receptor agonist and a corticosteroid and (ii) a second therapeutically active compound (i.e., a second ophthalmic compound) selected from the group consisting of an alpha 2 adrenergic receptor agonist, a corticosteroid, a lymphocyte function-associated antigen antagonist, a sodium channel blocker, a non-steroidal anti-inflammatory drug (NSAID), an antibiotic, and a combination thereof. In the compositions of the invention, the first ophthalmic compound is different from the second ophthalmic compound. For example, if the first ophthalmic compound is an alpha 2 adrenergic receptor agonist, then the second ophthalmic compound cannot be an alpha 2 adrenergic receptor agonist. Similarly, if the first ophthalmic compound is a corticosteroid, then the second ophthalmic compound cannot be a corticosteroid.

In one particular embodiment, the first therapeutically active compound is an alpha 2 adrenergic receptor agonist and the second therapeutic agent comprises a corticosteroid, a lymphocyte function-associated antigen antagonist, a sodium channel blocker, a non-steroidal anti-inflammatory drug (NSAID), an antibiotic, or a combination of two or more thereof.

Another embodiment of the invention provides a composition comprising corticosteroid in combination with a one or more of a second therapeutic agents such as a lymphocyte function-associated antigen antagonist, a sodium channel blocker, an alpha 2 adrenergic agonist, a non-steroidal anti-inflammatory drug (NSAID), and an antibiotic. Still another aspect of the invention provides a composition comprising an alpha 2 adrenergic receptor agonist in combination with one or more of the following components: (i) a lymphocyte function-associated antigen antagonist; (ii) a corticosteroid comprising loteprednol); (iii) a sodium channel blocker; (iv) a non-steroidal anti-inflammatory drug (NSAID); and (v) an antibiotic.

In some embodiments, compositions of the invention are heterogeneous solution formulations (e.g., a nanoemulsion), containing a combination of therapeutically effective amount of active pharmaceutical components in the formulation. In other embodiments, compositions of the invention are aqueous formulations, containing a combination of therapeutically effective amount of active pharmaceutical components in the formulation. As used herein, the term "nanoemulsion" refers to emulsion of oil-in-water that is about 250 nm or less, typically about 220 nm or less, and often about 200 nm or less in particle size or diameter. In other embodiments, such a small size nanoemulsion formulation also results in removal of any microbial organisms that may be present during the manufacturing process. This can be achieved, for example, by filtering the emulsion using 0.22 micron sterile filtration membranes during the production process. Once the nanoemulsion formulation is manufactured, the resulting product is stored and maintained as a sterile product, for example, either in single use containers such as blow fill seal (BFS) containers or preservative free multidose containers such as Aptar or Nemera container/closure.

In one embodiment, the formulations of the invention contain just two active ingredients or more than two active ingredients provided at least one of the active ingredient is an alpha 2 adrenergic receptor agonist and/or a corticosteroid.

One particular aspect of the invention provides a composition comprising two or more of the following pharmaceutically active compounds: (i) an alpha 2 adrenergic agonist; (ii) a corticosteroid; (iii) a lymphocyte function-associated antigen antagonist; (iv) a sodium channel blocker; (v) a non-steroidal anti-inflammatory drug; and (vi) an antibiotic, provided said composition comprises at least one of said alpha 2 adrenergic agonist or said corticosteroid. In one particular embodiment, said alpha 2 adrenergic agonist comprises brimonidine or a pharmaceutically acceptable salt thereof, or a combination thereof. In another embodiment, said corticosteroid comprises loteprednol etabonate, difluprednate, prednisone acetate, prednisolone sodium phosphate, triamcinolone, fluocinolone; fluorometholone, betamethasone, medrysone or a combination thereof.

Another aspect of the invention provides a composition comprising: (a) an alpha 2 adrenergic agonist or a pharmaceutically acceptable salt thereof; and (b) a second therapeutically active compound selected from the group consisting of: (i) a corticosteroid comprising loteprednol etabonate, difluprednate, prednisone acetate, prednisolone sodium phosphate, triamcinolone, fluocinolone; fluorometholone, betamethasone, medrysone; (ii) a lymphocyte function-associated antigen antagonist; (iii) a sodium channel blocker; (iv) a non-steroidal anti-inflammatory drug; (v) an antibiotic; and (iv) a combination of two or more thereof. In some embodiments, said composition is formulated as a heterogeneous aqueous solution. Yet in other embodiments, the heterogeneous aqueous solution comprises an emulsion. Still in other embodiments, the heterogeneous aqueous solution comprises and emulsion and a suspension. In further embodiments, the heterogeneous aqueous solution comprises an emulsion and a gel. Yet still in other embodiments, the heterogeneous aqueous solution comprises a suspension. In other embodiments, the heterogeneous aqueous solution comprises a gel. In yet other embodiments, said composition is formulated as a homogeneous aqueous solution. The composition can further comprise a pharmaceutically acceptable excipient. Typical pharmaceutically acceptable excipient comprises an emulsion stabilizing polymer, a water soluble polymer a surfactant, a tonicity modifier or a stabilizer, a viscosity modifier (e.g., carbopols), or a combination thereof. In some instances, said pharmaceutically acceptable excipient comprises polysorbate 80, Pemulen®, a polyol or a combination thereof. In other instances, said tonicity modifier or a stabilizer is selected from the group consisting of a polyol, a non-reducing disaccharide, and a combination thereof. In other embodiments, said lymphocyte function-associated antigen antagonist comprises N-{[2-(1-Benzofuran-6-ylcarbonyl)-5,7-dichloro-1,2,3,4-tetrahydro-6-isoquinolinyl]carbonyl}-3-(methylsulfonyl)-L-phenylalanine (i.e., lifitegrast). Yet in other embodiments, said alpha 2 adrenergic agonist comprises brimonidine, a pharmaceutically acceptable salt thereof or a combination thereof. Still in other embodiments, said corticosteroid comprises loteprednol etabonate. Still in other embodiments, said NSAID comprises ketorolac, diclofenac, flurbiprofen, bromfenac, nepafenac. Yet still in other embodiments, said sodium channel blocker comprises amiloride, amiloride analogues/derivatives, benzamil, benzamil analogues/derivatives, phenamil, phenamil analogues/derivatives, pyrazinoylguanidine analogues/derivatives. In other embodiments, said heterogeneous solution comprises castor oil, corn oil, olive oil, oleic acid or a combination thereof. In further embodiments, said second therapeutically active compound is selected from the group consisting of a sodium channel blocker, a corticosteroid, a lymphocyte function-associated antigen antagonist, an NSAID, an antibiotic and a combination of two or more thereof. Still in other embodiments, said second therapeutically active compound is selected from the group consisting of loteprednol etabonate, lifitegrast, a sodium channel blocker, an NSAID, an antibiotic and a combination of two or more thereof.

Yet another aspect of the invention provides an aqueous ophthalmic solution comprising: (a) an α2 adrenergic agonist; (b) a lymphocyte function-associated antigen antagonist; (c) an oil; and (d) a pharmaceutically acceptable excipient. In some embodiments, said pharmaceutically acceptable excipient comprises: (i) an emulsion stabilizing polymer, (ii) a surfactant, (iii) a tonicity modifier or a stabilizer selected from the group consisting of a polyol, a non-reducing disaccharide and a combination thereof, or (iv) a combination thereof. The composition can also include a viscosity modifying agent. In one particular embodiment, said lymphocyte function-associated antigen antagonist is lifitegrast. Yet in other embodiments, said α2 adrenergic agonist comprises brimonidine, a pharmaceutically acceptable salt thereof or a combination thereof.

Yet another aspect of the invention provides a composition comprising: (a) a corticosteroid; and (b) a second therapeutically active compound selected from the group consisting of (i) an alpha 2 adrenergic agonist or a pharmaceutically acceptable salt thereof (ii) a lymphocyte function-associated antigen antagonist; (iii) a sodium channel blocker; (iv) a non-steroidal anti-inflammatory drug; (v) an antibiotic; and (vi) a combination of two or more thereof. In some embodiments, the corticosteroid comprises any of loteprednol difluprednate, prednisone acetate, prednisolone sodium phosphate, triamcinolone, fluocinolone; fluorometholone, betamethasone, medrysone, or a combination thereof. In other embodiments, aid composition is formulated as a heterogeneous aqueous solution or a homogeneous aqueous solution. Still in other embodiments, the composition further comprises a pharmaceutically acceptable excipient. In one particular embodiment, the composition comprises loteprednol and at least one of the alpha 2 adrenergic agonist or a pharmaceutically acceptable salt thereof and sodium channel blocker. Suitable pharmaceutically acceptable excipient include an emulsion stabilizing polymer, a water soluble polymer a surfactant, a tonicity modifier or a stabilizer, a viscosity modifying agent, or a combination thereof. In one particular embodiment, said pharmaceutically acceptable excipient comprises polysorbate 80, Pemulen®, a polyol or a combination thereof. In some instances, said tonicity modifier or a stabilizer is selected from the group consisting of a polyol, a non-reducing disaccharide, and a combination thereof. In other instances, the lymphocyte function-associated antigen antagonist comprises N-{[2-(1-Benzofuran-6-ylcarbonyl)-5,7-dichloro-1,2,3,4-tetrahydro-6-isoquinolinyl]carbonyl}-3-(methylsulfonyl)-L-phenylalanine (lifitegrast). Yet in another embodiment, the alpha 2 adrenergic agonist is an alpha-2B adrenergic agonist. In some instances, said alpha 2 adrenergic agonist has a higher activity at the alpha-2A adrenergic receptor subtype compared to its activity at the alpha-2B receptor subtype. Yet in another particular embodiment, said alpha 2 adrenergic agonist comprises brimonidine, a pharmaceutically acceptable salt thereof or a combination thereof. In one particular embodiment, the sodium channel blocker comprises amiloride, amiloride analogues/derivatives, benzamil, benzamil analogues/derivatives, phenamil, phenamil analogues/derivatives, pyrazinoylguanidine analogues/derivatives. Still in another embodiment, said heterogeneous solution comprises castor oil, corn oil, olive oil, oleic acid or a combination thereof. In another embodiment, said second therapeutically active compound comprises a sodium channel blocker. Still in another embodiment, at least one other therapeutically active compound comprises an alpha 2 adrenergic agonist or a pharmaceutically acceptable salt thereof. Yet in other embodiments, said second therapeutically active compound comprises brimonidine, wherein the composition comprises a nanoemulsion.

Still another aspect of the invention provides an aqueous ophthalmic solution comprising: (a) a corticosteroid; (b) an alpha 2 adrenergic agonist, a lymphocyte function-associated antigen antagonist, an NSAID, an antibiotic or a sodium channel blocker, or a combination thereof; (c) an oil; and (d) a pharmaceutically acceptable excipient. In one embodiment, said pharmaceutically acceptable excipient comprises: (i) an emulsion stabilizing polymer, (ii) a surfactant, (iii) a tonicity modifier or a stabilizer selected from the group consisting of a polyol, a non-reducing disaccharide and a combination thereof, or (iv) a combination thereof. Yet in another embodiment, the corticosteroid comprises loteprednol and the lymphocyte function-associated antigen antagonist is lifitegrast. Still in another embodiment, the alpha 2 adrenergic agonist comprises brimonidine, a pharmaceutically acceptable salt thereof or a combination thereof.

Still yet another aspect of the invention provides an ophthalmic composition comprising a combination of an alpha 2 adrenergic agonist and a corticosteroid. In one particular embodiment, said alpha 2 adrenergic agonist comprises brimonidine tartrate. Yet in another embodiment, said corticosteroid comprises loteprednol etabonate. Still in another embodiment, said composition is an aqueous formulation. In some instances said aqueous formulation comprises nanoemulsion. Yet in other embodiments, said aqueous formulation comprises suspension or alpha 2 adrenergic agonist. In one particular embodiment, the amount of brimonidine tartrate in said composition ranges from 0.01% to 0.5% w/w. In another embodiment, the amount of loteprednol etabonate in said composition ranges from 0.01% to 0.5% w/w.

Compositions of the invention are useful for treatment of various eye disorders including, but not limited to, dry eye syndrome (keratoconjunctivitis sicca), sjogren's syndrome, congenital alacrima, xerophthalmia (dry eye from vitamin A deficiency), keratomalacia, thyroid eye disease, ocular rosacea, eyelid disorders, meibomian gland disease, meibomian gland dysfunction, ectropion, blepharitis, blepharochalasis, sarcoidosis, stye, hordeolum, chalazion, ptosis, pterygium, eyelid edema, eyelid dermatitis, trichiasis, madarosis, dacryoadenitis, stevens-johnson syndrome, ocular graft versus host disease, dacryocystitis, conjunctivitis, keratoconjunctivitis, blepharoconjunctivitis, blepharokeratoconjunctivitis, allergic conjunctivitis, vernal conjunctivitis, conjunctival suffusion, conjunctivochalasis, subconjunctival hemorrhage, pterygium, vernal keratoconjunctivitis, pinguecula, chemosis, iritis, iridocyclitis, anterior uveitis, glaucoma, red eye, keratitis, scleritis, episcleritis, peripheral ulcerative keratitis, neurotrophic keratitis, neurotrophic eye disease, corneal ulcer, ulcerative keratitis, corneal abrasion, photokeratitis, ultraviolet keratitis, exposure keratitis, superficial punctuate keratitis, thygeson's superficial punctuate keratopathy, herpes zoster keratitis, acne rosacea, corneal neovascularization, corneal dystrophy, epithelial basement membrane dystrophy, fuch's dystrophy, posterior polymorphous corneal dystrophy, macular corneal dystrophy, cyclitis, uveitis, iritis, post-operative inflammation following ocular surgery (i.e. eyelid surgery, cataract surgery, corneal surgery, refractive surgery including photorefractive keratectomy, glaucoma surgery, lacrimal gland surgery, conjunctival surgery, eye muscle surgery), ocular surface conditions caused by chemical burns, thermal burns or physical trauma, ocular conditions caused by the following autoimmune or vascular disorders: rheumatoid arthritis, juvenile rheumatoid arthritis, ankulosing spondylitis, reiter's syndrome, enteropathic arthritis, psoriatic arthritis, discoid and systemic lupus erythematosus, multiple sclerosis, graves' disease, antiphospholipid syndrome, sarcoidosis, wegner's granulomatosis, behcet's syndrome, polyarteritis *nodosa*, takayasu's arteritis, dermatomyositis, psoriasis, relapsing polychondritis, vasculitis, sickle cell-anemia, type II diabetes, diabetic retinopathy, and a combination thereof.

Some aspects of the invention provide a method for treating dry eye syndrome using the compositions disclosed herein. There are two major classes of dry eye syndrome: (i) aqueous tear-deficient dry eye (ADDE) and (ii) evaporative dry eye (EDE). There are also cases of mixed mechanism dry eye (i.e., both ADDE and EDE). ADDE is primarily due to failure of lacrimal tear secretion. ADDE can be further subdivided into Sjogren syndrome dry eye (where the lacrimal and salivary glands are targeted by an autoimmune process, e.g., rheumatoid arthritis) and non-Sjogren's syndrome dry eye (lacrimal dysfunction, but the systemic autoimmune features of Sjogren's syndrome are excluded, e.g., age-related dry eye). In contrast, EDE is primarily due to excessive water loss from the exposed ocular surface in the presence of normal lacrimal secretory function. Its causes can be extrinsic (e.g., ocular surface disorder due to some extrinsic exposure, contact lens wear or vitamin A deficiency) or intrinsic (e.g., Meibomian gland dysfunction and disorders of eyelid aperture). Meibomian glands secrete a mixture of lipids and other components that form the outer layer of the preocular tear film. This lipid layer functions to decrease tear film evaporation. Meibomian gland dysfunction (MGD) leads to evaporative dry eye disease. One of the most well-recognized clinic finding in MGD is the presence of numerous telangiectatic blood vessels coursing across the eyelid margin. MGD can also accompany tear-deficient dry eye disease, as seen in ocular graft-versus-host-disease (oGVHD). Other specific dry eye syndromes that can be treated using compositions of the invention include keratoconjunctivitis, dry eye caused by conjunctivitis, dry eye caused by allergic conjunctivitis, dry eye caused by blepharitis, dry eye caused by keratitis, dry eye caused by dacryoadenitis, dry eye caused by ocular rosacea, dry eye caused by boehm syndrome, dry eye caused by conjunctivochalasis, dry eye caused by blepharoconjunctivitis, dry eye caused by blepharokeratoconjunctivitis, dry eye caused by superficial punctuate keratitis, dry eye caused by thygeson's superficial punctuate keratopathy, dry eye caused by oGVHD, Sjogren's dry eye syndrome, dry eye caused by Stevens-Johnson syndrome, MGD, dry eye caused by meibomian gland disease, vitamin A deficiency induced dry eye, pharmacological induced dry eye (i.e. hormone replacement therapy, blood pressure medication, antihistamine, antidepressants, anticholinergic medications, glaucoma medication, antihypertensives, diuretics, sedatives, isotretinoin, nasal decongestants, oral contraceptives, beta-blockers, phenothiazines, atropine, pain relieving opiates), pregnancy induced dry eye, LASIK surgery or refractive surgery induced dry eye, dry eye induced by collagen vascular diseases (i.e. systemic lupus erythematosus, Wegener's granulomatosis, rheumatoid arthritis, relapsing polychondritis), dry eye caused by the infiltration of the lacrimal glands by tumors or sarcoidosis, dry eye caused by postradiation fibrosis of tear producing glands, dry eye caused by lacrimal gland, meibomian gland, or goblet cell ablation, dry eye caused by sensory denervation, dry eye caused by thermal or chemical burns, dry eye caused by underlying diabetic conditions, dry eye caused by viral, fungal, or bacterial infection, dry eye caused by prolonged contact lens use, dry eye caused by eyelid disorders or injury to the eyelid (i.e. bulging eyes, drooping eyelid), dry eye caused by corneal dystrophy, dry eye caused by autoimmune disorders, age-induced dry eye, and a combination thereof.

In some embodiments, methods for treating dry eye syndrome comprise treating a patient in need of a treatment for Meibomian gland dysfunction (MGD). In other embodiments, methods for treating dry eye syndrome comprise treating a patient in need of a treatment for aqueous tear-deficient dry eye (ADDE). In some instances, methods for treating ADDE comprise treating a patient in need of a treatment for Sjogren dry eye syndrome, ocular Graft-Versus-Host-Disease (oGVHD) or non-Sjogren dry eye syndrome. Yet in other embodiments, methods for treating dry eye syndrome comprise treating a patient in need of a treatment of evaporative dry eye (EDE). Still in other embodiments, methods of the invention include treating a patient in need of a treatment for mixed mechanism dry eye consisting of ADDE and EDE. Yet still in other embodiments, methods of the invention include treating a patient suffering from dry eye syndrome due to a complication of refractive eye surgery, or is attributable to one or more of the following causes: vitamin A deficiency, ocular surface disorders, allergy, aging, contact lens usage, medication usage or eyelid disorders.

In one particular aspect of the invention, a method is provided for treating an eye disorder, said method comprising administering to a subject in need of such a treatment a therapeutically effective amount of a composition in any of the compositions disclosed herein. In one embodiment, said eye disorder is selected from the group consisting of a dry eye syndrome; ocular graft-versus-host-disease; ocular rosacea; allergic conjunctivitis; autoimmune ocular surface disease; thygeson's superficial punctuate keratopathy; herpes zoster keratitis; Stevens-Johnson syndrome; keratitis; conjunctivitis; blepharitis; blepharochalasis; conjunctivochalasis; blepharoconjunctivitis; blepharokeratoconjunctivitis; post-operative inflammation or pain from ocular surgery; scleritis; episcleritis; anterior uveitis; iritis; cyclitis; ocular surface vascular disorder; ulcerative keratitis; photokeratitis; dacryocystitis; eyelid disorder; congenital alacrima; xerophthalmia; dacryoadenitis; vernal keratoconjunctivitis; pinguecula; and ocular surface disorder induced by chemical burns, thermal burns, or physical insult to the ocular surface. In some embodiment, said dry eye syndrome is selected from the group consisting of sjogren's syndrome, meibomian gland dysfunction and keratoconjunctivitis. In some instances, said eyelid disorder comprises eyelid inflammation, pain and/or edema. Still in other embodiments, said composition is administered topically to an eye of said subject.

Exemplary alpha 2 adrenergic receptor agonists that are useful in the present invention include, but are not limited to, brimonidine, 4-NEMD, 7-Me-marsanidine, agmatine, apraclonidine, cannabigerol, clonidine, detomidine, dexmedetomidine, fadolmidine, guanabenz, guanfacine, lofexidine, marsanidine, medetomidine, methamphetamine, mivazerol, rilmenidine, romifidine, talipexole, tizanidine, tolonidine, xylazine, xylometazoline, and the like including pharmaceutically acceptable salts thereof. In one particular composition of the present invention, the alpha 2 adrenergic receptor agonist is brimonidine (5-Bromo-N-(4,5-dihydro-1H-imidazol-2-yl) quinoxalin-6-amine), a pharmaceutically acceptable salt thereof or a combination thereof. "Pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, trifluoroacetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. Particular examples of pharmaceutically acceptable salts of brimonidine include, but not limited to, tartrate salt, trifluoroacetate salt, hydrochloric salt, acetate salt, oxalic acid salt, as well as others disclosed herein and/or known to one skilled in the art.

Alpha-2 adrenergic receptor agonists are those compounds that activate alpha-2 adrenergic receptors. There are three subtypes of this receptor, designated A, B, and C. An alpha-2 adrenergic receptor agonist that can activate any or all of these receptor subtypes can be used in the present invention. However, in some embodiments of the invention, an alpha 2 adrenergic receptor agonist having a higher activity or efficacy at the alpha-2A adrenergic receptor subtype compared to that at the alpha-2B receptor subtype (e.g., brimonidine and its salts) are used in the formulation. In some embodiments, the alpha 2 adrenergic agonist in compositions of the invention has a higher alpha 2A agonist activity compared to alpha 2B agonist activity. In some instances, the alpha 2A agonist activity of the alpha 2 adrenergic agonist is at least about 10% greater, typically at least about 20% greater and often at least about 30% greater than its alpha 2B agonist activity. As used in the context of the present invention, the term "about" when referring to a numeric value means±20%, typically ±10%, often ±5% and most often ±2% of the numeric value. In some preferred compositions of the present invention, alpha-2 adrenergic agonist is an alpha 2B adrenergic agonist. Typically, alpha 2B adrenergic agonist has higher alpha 2B agonist activity compared to its alpha 2A agonist activity. In some instances, the alpha 2B agonist activity of the alpha 2 adrenergic agonist is at least about 10% greater, typically at least about 20% greater and often at least about 30% greater than its alpha 2A agonist activity. Suitable alpha 2B adrenergic agonists lacking alpha 2a adrenergic agonist activity are known to one skilled in the art. Specific examples of suitable alpha 2B adrenergic agonist for the present invention include, but are not limited to those disclosed in U.S. Pat. Nos. 6,787,517, 7,345,065, 8,575,207, 9,193,690, 9,522, 150, 9,289,420, 9,545,394, and 9,555,021 which are incorporated herein by reference in their entirety, as well as those known to one skilled in the art.

Compositions of the invention also include a lymphocyte function-associated antigen antagonist. Lymphocyte function-associated antigen (LFA)-1/intercellular adhesion molecule (ICAM)-1 interactions mediate several important steps in the evolution of an immune response. Exemplary lymphocyte function-associated antigen antagonists include, but are not limited to, lifitegrast (i.e., (S)-2-(2-(benzofuran-6-carbonyl)-5,7-dichloro-1,2,3,4-tetrahydroisoquinoline-6-carboxamido)-3-(3-(methylsulfonyl)phenyl)propanoic acid), which is a water-soluble drug that blocks LFA-1 from binding to ICAM-1, and other lymphocyte function-associated antigen antagonists that are known to one skilled in the art. Any lymphocyte function-associated antigen can be used in compositions of the invention.

In some embodiments, compositions of the invention are formulated as an aqueous solution, which can be a homogeneous or heterogeneous solution. In such embodiments, compositions of the invention include at least two active ingredients. In one particular embodiment, the formulation contains at least one active ingredient that is a water soluble and at least one other active ingredient that is a lipophilic. Still in other embodiments, compositions of the invention are formulated as an aqueous ophthalmic solution. As stated above, the aqueous ophthalmic solution can be homogenous or heterogeneous and can include aqueous suspension or dispersion, where at least some of the active ingredients are present as suspension or dispersion in aqueous solution. The aqueous ophthalmic solution can be a substantially homogeneous aqueous solution, where substantially all (i.e., ≥85%, typically ≥90%, often ≥95%, and most often ≥99%) of the active ingredients are dissolved in the aqueous solution.

In one particular embodiment, one of the active ingredients is brimonidine, its pharmaceutically acceptable salt thereof or a combination thereof. The composition includes a second active ingredient that can be lifitegrast. As used herein, the term "active ingredient" refers to a compound that is primarily used to treat eye disorder, e.g., dry eye syndrome. Thus, while water and oil can be present in some formulations, they are not used primarily for the purpose of treating eye disorder but are used as a vehicle to carry active ingredients. In some embodiments, the term "active ingredient" refers to: an alpha 2 adrenergic agonist; a lymphocyte function-associated antigen antagonist; a corticosteroid; and/or a sodium channel blocker. Other ingredients that may be present in formulations/compositions of the invention are used primarily as pharmaceutically acceptable excipients or vehicles, such as a pH adjusting agent, a tonicity modifier or a stabilizer, a surfactant, an emulsion stabilizer, etc.

A therapeutically effective amount of an active ingredient in the composition of the invention can be readily determined by one skilled in the art. In some embodiments, the composition of the invention is formulated as a heterogeneous aqueous solution. In one particular embodiment, the composition of the invention include from about 0.01 to about 5 mg/mL (about 0.001% to about 0.5% w/v) typically about 0.2% w/v or less (e.g., 0.05-0.2% often 0.07-0.15%) of brimonidine or a salt thereof (e.g., brimonidine tartrate and hydroxy brimonidine trifluoroacetate). The ingredient amounts are presented in units of either % weight/volume (% w/v) or weight/weight (% w/w). In one specific embodiment, brimonidine tartrate is used as an alpha 2 adrenergic agonist. In one embodiment, the amount of brimonidine tartrate present in the composition is from about 0.01% w/w to about 1% w/w, typically from 0.01% w/w to about 0.7% w/w, and often from about 0.02% to about 0.5% w/w. In one particular embodiment, the amount of brimonidine tartrate present in the composition is from about 0.05 w/w/to about 0.5 w/w.

Still in another embodiment, the lymphocyte function-associated antigen antagonist used in compositions of the invention is lifitegrast. In some embodiments, the amount of lifitegrast present in compositions of the invention is from about 0.1% w/w to about 20% w/w, typically from about 0.2% w/w to about 15% w/w, and often from about 0.3% w/w to about 10% w/w.

Yet in some embodiments, the composition of the invention also includes a corticosteroid. Exemplary corticosteroids include, but are not limited to, methylprednisolone, hydrocortisone, betamethasone, dexamethasone and loteprednol etabonate. In one particular embodiment, the corticosteroid used in the composition of the invention is loteprednol etabonate. In some embodiments, the amount of loteprednol etabonate present in the compositions of the invention is from about 0.01% w/w to 2% w/w; typically from about 0.05% w/w to 1%, and often from about 0.1% to about 0.3%.

Compositions of the invention can also include a sodium channel blocker and/or mucolytic agents. Suitable sodium channel blockers and/or mucolytic agents for treatment of eye disorder are known to one skilled in the art and include those disclosed, for example, in U.S. Pat. Nos. 9,655,896, 9,586,911, 9,346,753, 8,980,898, 8,673,340, 8,058,278, 7,875,619, 7,868,010, 7,842,697, 7,820,678, 7,807,834, 7,410,968, 7,399,766, 7,388,013, 7,375,107, 7,368,451, 7,368,450, 7,368,447, 7,375,107, 7,368,451, 7,368,450, 7,368,447, 7,345,044, 7,332,496, 7,317,013, 7,247,637, 7,247,636, 7,241,766, 7,192,960, 7,192,959, 7,192,958, 7,189,719, 7,186,833, 7,064,129, 7,030,177, 7,026,325, 6,995,160, 6,903,105, 6,858,615, and 6,858,614 and, in PCT Publication Nos. WO2003/070182, WO2003/070184, WO2004/0732629, WO2005/025496, WO2005/016879, WO2005/018644, WO2006/022935, WO2006023573, WO2006/023617, WO2007/018640, WO2007/146869, WO2008/031028, and WO2008/031048 which are incorporated herein by reference in their entirety. Specific examples of suitable sodium channel blockers for the present invention include, but are not limited to amiloride, benzamil, phenamil, and amiloride analogues as exemplified by U.S. Pat. Nos. 9,655,896, 9,586,911, 9,346,753, 8,980,898, 8,673,340, 8,058,278, 7,875,619, 7,868,010, 7,842,697, 7,820,678, 7,807,834, 7,410,968, 7,399,766, 7,388,013, 7,375,107, 7,368,451, 7,368,450, 7,368,447, 7,375,107, 7,368,451, 7,368,450, 7,368,447, 7,345,044, 7,332,496, 7,317,013, 7,247,637, 7,247,636, 7,241,766, 7,192,960, 7,192,959, 7,192,958, 7,189,719, 7,186,833, 7,064,129, 7,030,177, 7,026,325, 6,995,160, 6,903,105, 6,858,615, and 6,858,614 and, in PCT Publication Nos. WO2003/070182, WO2003/070184, WO2004/0732629, WO2005/025496, WO2005/016879, WO2005/018644, WO2006/022935, WO2006023573, WO2006/023617, WO2007/018640, WO2007/146869, WO2008/031028, and WO2008/031048.

In another embodiment, compositions of the invention can also include a non-steroidal anti-inflammatory drug (i.e., NSAID). Suitable NSAIDs that are useful in treating eye disorder include ketorolac (0.05 to 0.3%), diclofenac (0.01 to 1%), flurbiprofen (0.01 to 1%), bromfenac (0.01 to 0.5%), nepafenac (0.05 to 0.5%), etc. Some of these are commercially available as Acular, Acular PF, and Acular LS (ketorolac tromethamine, Allergan), Ocufen (flurbiprofen sodium, Allergan), Voltaren (diclofenac sodium, Novartis), Xibrom (bromfenac ophthalmic solution, Ista Pharmaceuticals), Prolensa (bromfenac ophthalmic solution, Bausch & Lomb) and Nevanac (nepafenac, Alcon).

In some embodiments, compositions of the invention are used as an ophthalmic formulation. Such ophthalmic formulations can be homogeneous or heterogeneous formulations. In such embodiments, the formulated composition contains an oil or a fatty acid ester. A fatty acid ester has the meaning commonly understood in the art, being an ester formed between an alcohol and a fatty acid. Exemplary fatty acid esters that are useful in formulations of the invention include, but are not limited to, triglyceride esters commonly known as vegetable oils, mono and diglyceride esters of fatty acids, fatty acid methyl esters, as well as other fatty acid esters that are known to one skilled in the art. It should be appreciated the fatty acid ester can be a mixture of several chemical compounds or an essentially pure compound. Typically, the fatty acid ester is a vegetable oil. Particular examples of vegetable oils that can be used include, but are not limited to, castor oil, sesame oil, soybean oil, cottonseed oil, olive oil, peanut oil, safflower oil, sunflower oil, palm oil, palm kernel oil, canola oil, and Miglyol Oil®. In one particular embodiment, the fatty acid ester is castor oil.

Various vehicles can be used in the ophthalmic formulations of the present invention. These vehicles include, but are not limited to, purified water (water), polyvinyl alcohol, povidone, hydroxypropyl methyl cellulose, poloxamers, carboxymethyl cellulose, hydroxyethyl cellulose, cyclodextrin and a mixture of two or more thereof. The vehicle is used in the formulation in amounts as needed to provide the concentration of the active compound(s) disclosed herein. In one particular embodiment, the vehicle comprises water.

In some embodiments of this invention, an emulsion stabilizing polymer is used. While not intending to limit the scope of the invention, emulsion stabilizing polymers generally contain hydrophilic groups such as cellulose, sugars, ethylene oxide, hydroxide, carboxylic acids or other polyelectrolytes. Without being bound by any theory, it is believed that these polymers help to stabilize emulsions by increasing the viscosity of the formulation as well as by reducing the interfacial tension. Some examples of emulsion stabilizing polymers useful in this invention include, but are not limited to, carbomers, Pemulen®, sodium carboxymethylcellulose, hydroxypropylmethylcellulose, povidone, polyvinyl alcohol, polyethylene glycol and a mixture of two or more thereof.

In one particular embodiment, Pemulen® (B.F. Goodrich, Cleveland, Ohio) is used as the polymeric based stabilizer. Pemulen® are Acrylates/$C_{10-30}$ Alkyl Acrylate Cross-Polymers.

In another embodiment of this invention, the formulation comprises a surfactant. Without being bound by any theory, a surfactant is used to help facilitate the formation of the emulsion and improve its stability. Any type of surfactant can be used including, anionic, cationic, amphoteric, zwitterionic, nonionic, as well as a mixture of two or more thereof. In one particular embodiment, the formulation of the invention comprises a nonionic surfactant. Exemplary nonionic surfactants include, but are not limited to, polysorbates, poloxamers, alcohol ethoxylates, ethylene glycol-propylene glycol block copolymers, fatty acid amides, alkylphenol ethoxylates, phospholipids, and two or mixture thereof. In one particular embodiment, the surfactant is Polysorbate 80 (ICI Americas, Inc., Wilmington, Del.).

Various buffers and means for adjusting pH can be used so long as the resulting preparation is ophthalmically acceptable. Accordingly, useful buffers include, but are not limited to, acetate buffers, citrate buffers, phosphate buffers and borate buffers. In one particular embodiment, a buffering agent is used to maintain the pH in the therapeutically useful range of pH 4-10, typically about pH 5-8, often a pH range of 6.5-8.0, more often a pH range of 7.0-8.0, and most often a pH range of 7.2-7.6. It should be appreciated, however, that the scope of the invention is not limited to these particular pH ranges. In general, any pH range that provides suitable penetration of the active ingredient(s) through the eye can be used. Typically, a buffering agent known to those skilled in the art is used including, but not limited to, acetate, borate, tris, carbonate, citrate, histidine, succinate, and phosphate. In one particular embodiment, the buffering agent comprises boric acid. In another embodiment, the buffering agent comprises sodium citrate.

To provide the ophthalmic formulations with a pH substantially corresponding to the pH of the fluids of the eye or at an acceptable physiological pH, as described above, the pH of the ophthalmic formulation can be adjusted by addition of an acid or a base in quantity sufficient to achieve the desired pH. The pH adjustment can be achieved through use of various chemicals such as hydrochloric acid, sodium hydroxide, citric acid, sodium citrate, acetic acid, sodium acetate, ammonium acetate, succinic acid, lactic acid, calcium lactate, sodium lactate, sodium fumarate, sodium propionate, boric acid, tris base, ammonium borate, maleic acid, phosphoric acid, sulfuric acid and aluminum potassium sulfate and the like. A specific example of an acid that can be used to adjust the pH of the aqueous buffered ophthalmic formulation is 1 N hydrochloric acid. A specific example of a base that can be used to adjust the pH of the aqueous buffered ophthalmic formulation is 1 N sodium hydroxide. However, it should be appreciated that the scope of the invention is not limited to this particular acid and base. In general, any pharmaceutically acceptable acids and bases can be used to adjust the pH. In one particular embodiment, the ophthalmic formulations of the present invention contain a combination of dibasic and monobasic phosphate or boric acid and sodium borate—as buffering agents. For example, the formulations contain an amount of boric acid and sodium borate sufficient to buffer the formulation in a pH range of 6.5-8.0 or 7.5-8.0 or dibasic and monobasic phosphate sufficient to buffer the formulation in a pH range of 6.5-8.0 or 7.0-8.0 or 7.5-8.0.

In another embodiment, a tonicity agent (tonicity-adjusting agent) is used to adjust the composition of the formulation to the desired isotonic range. The tonicity-adjusting agent can be a polyol or a disaccharide including non-reducing disaccharides. Such tonicity agents are known to one skilled in the art, and include, but are not limited to, glycerin, mannitol, sorbitol, trehalose, xylitol, sodium chloride, and other electrolytes. In one particular embodiment, the tonicity agent is glycerin.

If desired, gum and/or resin can be included in the formulations of the invention, including for example, sodium polyacrylate, cellulose ether, calcium alginate, carboxyvinyl polymer, ethylene-acrylic acid copolymer, vinyl pyrrolidone polymer, vinyl alcohol-vinyl pyrrolidone copolymer, nitrogen-substituted acrylamide polymer, polyacrylamide, cationic polymer such as cationic guar gum, dimethylacrylic ammonium polymer, acrylic acid-methacrylic acid copolymer, polyoxyethylene-polypropylene copolymer, polyvinyl alcohol, pullulan, agar, gelatine, chitosan, polysaccharide from tamarindo seed, xanthan gum, caragenan, high-methoxyl pectin, low-methoxyl pectin, guar gum, acacia gum, microcrystalline cellulose, arabinogalactan, karaya gum, tragacanth gum, alginate, albumin, casein, curdlan, gellan gum, dextran, cellulose, polyethyleneimine, high polymerized polyethylene glycol, cationic silicone polymer, synthetic latex, acrylic silicone, trimethylsiloxysilicate and fluorinated silicone resin.

In some embodiments, the formulations are preservative-free. In other embodiments, a preservative is used. Preservatives are used, for example, to prevent bacterial contamination in multiple-use ophthalmic preparations. Exemplary preservatives include, but are not limited to, benzalkonium chloride, stabilized oxychloro complexes (otherwise known as Purite®), phenylmercuric acetate, chlorobutanol, benzyl alcohol, parabens, and thimerosal. In one particular embodiment, the preservative is Purite®.

Other excipient components or ingredients that can also be included in the ophthalmic formulations of the present invention are chelating agents and antibiotics. Suitable chelating agents are known in the art. Particular examples of useful chelating agents include, but are not limited to, edetate salts like edetate disodium, edetate calcium disodium, edetate sodium, edetate trisodium, and edetate dipotassium. In one particular embodiment, the chelating agent is edentate disodium. It should be appreciated that other chelating agents may also be used in place of or in conjunction with edetate disodium. Some examples of antibiotics that can be included in formulations of the invention include, but are not limited to, trimethoprim sulfate/polymyxin B sulfate, gatifloxacin, moxifloxacin hydrochloride, tobramycin, teicoplanin, vancomycin, azithromycin, clarithromycin, amoxicillin, penicillin, ampicillin, carbenicillin, ciprofloxacin, levofloxacin, amikacin, gentamicin, kanamycin, neomycin and streptomycin.

The formulations of the present invention can be packaged in various package forms known in the field of topical ophthalmics. In one embodiment, the formulation is packaged in sterile, preservative-free single-use packs or vials or containers (i.e., the unit dose vials). Each vial, for example as small as a 0.9 mL, may be made of low density polyethylene so as to contain a small quantity of the formulation, e.g., 0.2-0.4 for a single use. This way, where the pharmaceutical composition is sterilized and contained in disposable single-dose containers for topical use in drop form, multiple vials in the form of a set of 30 vials, 60 vials and so on can be packaged in a tray with a lid, for example, a polypropylene tray with an aluminum peelable lid. The entire contents of each tray can be dispensed intact, and one vial or pack is used each time and immediately discarded after each use. For example, plastic ampules or vials or containers can be manufactured using blow-fill-seal (BFS) technology. The BFS processes may involve plastic extrusion, molding, aseptic filling, and hermetic sealing in one sequential operation and those processes are known in the art. In another embodiment, the formulation is packaged in multi-dose vials such that the materials can be dispensed as sterile at each time using specialized container/closure maintaining the sterility integrity. In yet another embodiment, the formulation is packed in conventional vials/containers as sterile product.

In some embodiments, the dosage form of the invention is eye drops of heterogeneous aqueous solution, eye drop formulations containing two or more active ingredients in which the first active ingredient is an alpha 2 adrenergic receptor agonist and a second active ingredient is selected from the group consisting of a lymphocyte function-associated antigen antagonist, a corticosteroid, a sodium channel blocker, a non-steroidal anti-inflammatory drug, an antibiotic and a combination of two or more thereof. For example, an eye drop formulations can contain brimonidine or brimonidine tartrate and loteprednol, or brimonidine or brimonidine tartrate and lifitegrast, or brimonidine or brimonidine tartrate and sodium channel blocker, or brimonidine or brimonidine tartrate and an NSAID, or brimonidine or brimonidine tartrate and an antibiotic. In still some embodiments, the dosage form of the invention is eye drops of heterogeneous aqueous solution, eye drop formulations containing two or more active ingredients in which the first active ingredient is an corticosteroid and a second active ingredient is selected from the group consisting of a lymphocyte function-associated antigen antagonist, an alpha 2 adrenergic agonist, a sodium channel blocker, an NSAID, an antibiotic and a combination of two or more thereof. For example, an eye drop formulations can contain loteprednol and brimonidine or brimonidine tartrate, or loteprednol and lifitegrast, or loteprednol and a sodium channel blocker, or loteprednol and an NSAID, or loteprednol and an antibiotic. Eye drops typically contain, according to the invention, aqueous/oily suspensions of the active ingredients in pharmaceutically acceptable carriers and/or excipients. In some embodiments, the mean particle size of the active ingredient employed is about 20 μm or less, typically 10 μm or less, often 1 μm or less, more often 0.5 μm or less, still more often 0.2 μm or less and most often 0.15 μm or less In another aspect, the invention relates to methods of treating a subject or human patient suffering from an eye disorder (e.g., dry eye syndrome) by administering to the eye of the patient an ophthalmic formulation disclosed herein. In some embodiments, formulations used in treating an eye disorder contain (i) brimonidine or a pharmaceutically acceptable salt thereof (e.g., brimonidine tartrate) and lifitegrast, (ii) brimonidine or a pharmaceutically acceptable salt thereof (e.g., brimonidine tartrate) and loteprednol (iii) a corticosteroid (e.g., loteprednol) and a sodium channel blocker, (iv) brimonidine or a pharmaceutically acceptable salt thereof (e.g., brimonidine tartrate) and sodium channel blocker, (v) a corticosteroid (e.g., loteprednol) and lifitegrast, (vi) a corticosteroid (e.g., loteprednol) and an NSAID, (vii) a corticosteroid (e.g., loteprednol) and an antibiotic, (viii) brimonidine or a pharmaceutically acceptable salt thereof (e.g., brimonidine tartrate) and an NSAID, or (viii)

brimonidine or a pharmaceutically acceptable salt thereof (e.g., brimonidine tartrate) and an antibiotic. In one particular embodiment, compositions of the invention include brimonidine or a pharmaceutically acceptable salt thereof and loteprednol; a combination of brimonidine or a pharmaceutically acceptable salt thereof and a sodium channel blocker; a combination of brimonidine or a pharmaceutically acceptable salt thereof and lifitegrast; a combination of loteprednol and a sodium channel blocker; a combination of loteprednol and lifitegrast; a combination of loteprednol and an antibiotic; or a combination of loteprednol and an NSAID.

The active ingredients are present in an amount effective to provide a desired therapeutic benefit to a patient suffering from an eye disorder to whom the composition is administered. The therapeutically effective amount should be sufficient to realize relief from the eye disorder after the treatment. The eye of a subject or human patient can be the entire eye structure or a tissue or gland in or around the eye such as the ocular tissue, eyelids, margin of the eyelid of the subject, ocular surface. The ophthalmological pharmaceutical formulation is topically administrable and/or is administered in, on or around the eye. The dry eye syndrome can be aqueous tear-deficient dry eye (ADDE) or evaporative dry eye (EDE) or consists of both ADDE and EDE (mixed mechanism dry eye). ADDE may be Sjogren syndrome dry eye (where the lacrimal and salivary glands are targeted by an autoimmune process, e.g., rheumatoid arthritis) and non-Sjogren's syndrome dry eye (lacrimal dysfunction, but the systemic autoimmune features of Sjogren's syndrome are excluded, e.g., age-related dry eye). The actual dose of the active compounds of the present invention depends on the specific compound, and on the condition to be treated; the selection of the appropriate dose is well within the knowledge of the skilled artisan.

A preferred composition contains an ophthalmically active corticosteroid (e.g., loteprednol, difluprednate, prednisone acetate, prednisolone sodium phosphate, triamcinolone, fluocinolone; fluorometholone, betamethasone, medrysone, and a combination these compounds) and at least one other therapeutically active compound. The second therapeutically active compound can be an alpha 2 adrenergic agonist or a pharmaceutically acceptable salt thereof, a lymphocyte function-associated antigen antagonist or a sodium channel blocker, and/or mucolytic agents. Suitable sodium channel blockers and/or mucolytic agents are known to one skilled in the art. Examples of suitable sodium channel blockers that can be used in the composition of the present invention are amiloride, amiloride analogues/derivatives, benzamil, benzamil analogues/derivatives, phenamil, phenamil analogues/derivatives, pyrazinoylguanidine analogues/derivatives). An example of suitable lymphocyte function-associated antigen antagonist that can be used in the composition of the present invention is N-{[2-(1-Benzofuran-6-ylcarbonyl)-5,7-dichloro-1,2,3,4-tetrahydro-6-isoquinolinyl]carbonyl}-3-(methylsulfonyl)-L-phenylalanine (lifitegrast). An alpha 2 adrenergic agonist or a pharmaceutically acceptable salt thereof can be an alpha-2A or alpha-2B adrenergic agonist which agonist have been exemplified herein. The compositions of the present invention can include other second therapeutically active compounds known to one skilled in the art such as a non-steroidal anti-inflammatory drug (NSAID) including ketorolac, diclofenac, flurbiprofen, bromfenac, nepafenac; an antibiotic including trimethoprim sulfate/polymyxin B sulfate, polymyxin B/bacitracin, polymyxin B/neomycin/gramicidin, polymyxin B/neomycin/bacitracin, gatifloxacin, moxifloxacin hydrochloride, tobramycin, teicoplanin, vancomycin, azithromycin, clarithromycin, amoxicillin, penicillin, ampicillin, carbenicillin, ciprofloxacin, levofloxacin, amikacin, gentamicin, kanamycin, neomycin and streptomycin, besifloxacin, ciprofloxacin, moxifloxacin, ofloxacin, gatifloxacin, erythromycin, bacitracin. The composition can be formulated as a heterogeneous aqueous solution such as a nanoemulsion or as a homogeneous aqueous solution. The heterogeneous solution preferably contains castor oil, corn oil, olive oil, oleic acid or a combination of these components. The composition can contain a pharmaceutically acceptable excipient including an emulsion stabilizing polymer, a water-soluble polymer a surfactant, a tonicity modifier or a stabilizer, polysorbate 80, Pemulen®, a polyol, a viscosity modifying agent, or a combination of these. It should be appreciated that in some instances, a particular excipient may have one or more utility. For example, a viscosity modifying agent can also have tonicity modifier property, a tonicity stabilizing property, emulsion stabilizing proper, or a combination thereof. Preferably, the composition contains loteprednol and at least one of the alpha 2A or 2B adrenergic agonist or a pharmaceutically acceptable salt thereof, lifitegrast and a sodium channel blocker in a pharmaceutically acceptable excipient.

Another preferred composition of the present invention is an aqueous ophthalmic solution containing an ophthalmically active corticosteroid (e.g., loteprednol, difluprednate, prednisone acetate, prednisolone sodium phosphate, triamcinolone, fluocinolone; fluorometholone, betamethasone, medrysone, and a combination these compounds); an alpha 2 adrenergic agonist, a lymphocyte function-associated antigen antagonist, a sodium channel blocker, an NSAID, an antibiotic or a combination of these compounds; an oil and a pharmaceutically acceptable excipient. In one composition, ophthalmically active corticosteroid is limited to loteprednol. Any of these compositions (formulated as a homogeneous ophthalmic aqueous formulation, a heterogeneous ophthalmic aqueous solution, a hydrogel, or an ophthalmic cream) can contain a pharmaceutically acceptable excipient. The pharmaceutically acceptable excipient can include any of or a combination of an emulsion stabilizing polymer, a surfactant, a tonicity modifier or a stabilizer (e.g., polyol, a non-reducing disaccharide or both) and/or a viscosity modifying agent. The heterogeneous ophthalmic aqueous solution can be an emulsion (e.g., a nanoemulsion), suspension or a combination of an emulsion and suspension. Still in other embodiments, the composition has a corticosteroid containing loteprednol and lifitegrast in a pharmaceutically acceptable excipient. Any of the eye disorders specified herein can be treated in a subject (e.g., a human patient) by administering to a subject in need of such a treatment a therapeutically effective amount of any of the compositions, preferably nanoemulsions or aqueous solutions, described herein.

Any of the above-described compositions can be used for treating an eye disorder specified herein by administering to a subject (e.g., a human patient) in need of such a treatment a therapeutically effective amount of a given composition preferably nanoemulsion or aqueous solution, described herein. Preferred eye disorders for treatment include a dry eye syndrome (e.g., sjogren's syndrome, meibomian gland dysfunction and keratoconjunctivitis); ocular graft-versus-host-disease; ocular rosacea; allergic conjunctivitis; autoimmune ocular surface disease; thygeson's superficial punctuate keratopathy; herpes zoster keratitis; Stevens-Johnson syndrome; keratitis; conjunctivitis; blepharitis; blepharochalasis; conjunctivochalasis; blepharoconjunctivitis; blepharokeratoconjunctivitis; post-operative inflammation or pain from ocular surgery; scleritis; episcleritis; anterior uveitis; iritis; cyclitis; ocular surface vascular disorder; ulcerative keratitis; photokeratitis; dacryocystitis; eyelid disorder; congenital alacrima; xerophthalmia; dacryoadenitis; vernal keratoconjunctivitis; pinguecula; and ocular surface disorder induced by chemical burns, thermal burns, or physical insult to the ocular surface eyelid inflammation, pain and/or edema. Preferably, the composition is administered topically to an eye of said subject. The composition is formulated as a homogeneous ophthalmic aqueous formulation, a heterogeneous ophthalmic aqueous solution, a hydrogel, or an ophthalmic cream.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

As used herein, the term "about" is not intended to limit the scope of the invention but instead encompass the specified material, parameter or step as well as those that do not materially affect the basic and novel characteristics of the invention. When referring to a numeric value, the term "about" or "approximately" as used herein refers to being within an acceptable error range for the particular value as determined by one of ordinary skill in the art, which will depend in part on how the value is measured or determined, i.e., the limitations of the measurement system, i.e., the degree of precision required for a particular purpose. For example, the term "about" can mean within 1 or more than 1 standard deviation, per the practice in the art. Alternatively, the term "about" when referring to a numerical value can mean±20%, typically ±10%, often ±5% and more often ±1% of the numerical value. In general, however, where particular values are described in the application and claims, unless otherwise stated, the term "about" means within an acceptable error range for the particular value. Moreover, any numerically value is to be understood to be within the one standard deviation unit per the practice in the art.

An example of a topical heterogeneous ophthalmic solution with its various components (w/w) useful for treating an eye disorder (e.g., dry eye syndrome) is as follows: brimonidine tartrate in the amount of 0.02% to 0.2% by weight, surfactant such as Polysorbate 80 at about 0.02%-2% by weight or poloxamer/tyloxapol at about 0.1% and 0.25% by weight; carbomer copolymer (type A or type B) about 0.05% by weight; tonicity agent (glycerine or includes glycerine about 2.2% by weight; citrate/tris buffer of pH 6.0-8.0; sodium EDTA in the amount of about 0.02% or less by weight; an oil (e.g., castor oil) in the amount of about 1.25% by weight. Alternatively, the oil for the oil phase is a medium chain triglyceride in the range from 0.5-4%, typically at about 2%. To prepare this formulation, all water-soluble components can be added and heated (about 60-70° C.) to make water the phase with buffer. A lipophilic solution is prepared using a lipophilic solvent (e.g., castor oil) and heating to about 60-70° C. Heterogeneous solution is formed by rapid addition of lipophilic solution into water phase followed by high shear mixing. The final solution is sterilized via 0.22 micron filter. Alternatively, sterilization can also be done by autoclaving at about 121° C. for 20 min. Alternatively, sterilization can also be done by gamma or e beam irradiation. The sterilized heterogeneous solution is filled into single dose disposable tubes by BFS technology or the like or into multi dose container/closure.

One particular embodiment for preparing a heterogeneous aqueous solution comprising a composition of the invention is described below:
1. Mix Oil phase: Mix appropriate amounts of castor oil and polysorbate 80 until uniformity is obtained;
2. Mix Aqueous phase: Mix required amounts of Pemulen, water and glycerin until uniformity is obtained
3. Perform primary mixing of oil and aqueous phase mixtures from steps 1 and 2;
4. Perform high shear mixing and homogenization of mixture from step 3;
5. Confirm the ophthalmic solution properties via in process testing A topical ophthalmic aqueous solution with its various components (w/w) useful for treating an eye disorder (e.g., dry eye syndrome) can also be prepared as described below. In this particular process, the resulting formulation often contains colloid particles with an average particle size of equal to or less than 0.2 μm and greater than 0.02 μm and has an oily core surrounded by an interfacial film. The size population distribution of the colloidal particles may be monomodal. The solution contains anywhere from 0.05% to 0.2% (e.g., 0.075%) alpha 2 adrenergic receptor agonist (e.g., brimonidine or a salt thereof) in weight to the total weight (w/w) of the ophthalmic solution, 0.5 to 4% w/w (e.g., 2% w/w) medium-chain triglycerides, 0.02% w/w benzalkonium chloride or no benzalkonium (preservative-free) for single dose sterile containers, and surfactants. The surfactants, for example, consist of a mixture of tyloxapol in an amount of 0.3% w/w and poloxamer in an amount of 0.1% w/w. The ophthalmic solution can include one or more oils selected from, castor, olive, soy, corn, mineral, cottonseed, safflower and sesame. The solution does not contain any significant amount (≤1%, typically ≤0.5%, often ≤0.1% and most often ≤0.01%) of substances capable of generating a negative charge and/or phospholipids. The ophthalmic heterogeneous solution can be used for treating a dry eye syndrome.

Another process for preparing a topical ophthalmic aqueous solution with its various components (w/w) useful for treating an eye disorder is described as follows. In this particular process, the formulation contains brimonidine tartrate in an amount of about 0.02%; lifitegrast from 0.3% to 10% by weight, preferably 3% by weight, polysorbate 80 (e.g., about 1.0% by weight); acrylate/C10-30 alkyl acrylate cross-polymer (about 0.05% by weight); water q.s.; and castor oil in an amount of about 1.25% by weight. The alpha 2 adrenergic receptor agonist and lifitegrast are the only pharmaceutically active agents present in this particular topical ophthalmic solution. However, this formulation also include a tonicity agent or a demulcent component (e.g., glycerine, which can be in an amount of about 2.2% by weight), a buffer. The pH of this topical ophthalmic solution may be in the range of about 6.0 to about 8.0. The topical ophthalmic solution is therapeutically effective in increasing tear production.

Yet another example of a topical ophthalmic solution with its various components (w/w) is as follows. This particular formulation includes brimonidine tartrate in an amount ranging from about 0.01% to about 0.5%, typically in an amount of about 0.075% by weight; lifitegrast from 0.3% to 10% by weight, typically 3% by weight, carbomer homopolymer type B in an amount ranging from about 0.2 to about 0.6%, typically in an amount of about 0.4% or about 0.25%, and/or carbomer homopolymer type C in an amount ranging from about 0.4 to about 5% typically in an amount of about 4% or about 2.5%, and/or polycarbophil in an amount ranging from about 0.2% to about 0.5% typically in an amount of about 0.4% or about 0.2%; glycerin in an amount ranging from about 0.5% to about 1% typically in an amount of about 0.9%; benzalkonium chloride in an amount ranging from about 0.003% to about 0.01% typically in an amount of about 0.007%; edetate sodium in an amount ranging from about 0.03% to about 0.07% typically in an amount of about 0.05%; sodium chloride in an amount of up to about 0.09%, typically in an amount of about 0.06% or q.s. to isotonicity, or mannitol q.s. to isotonicity, or without isotonicity adjustors sodium chloride and mannitol; propylene glycol in an amount ranging from about 0.3% to about 0.6% typically in an amount of about 0.5%; water q.s., to 100 gms and sodium hydroxide or hydrochloric acid q.s., to adjust pH to 7.8. The topical ophthalmic solution is therapeutically effective for treating dry eye syndrome. Although preservatives such as benzalkonium chloride can be used in the formulations of the present invention as described in the non-limiting examples, typically the formulations are preservative-free.

Another example of a topical ophthalmic formulation with its various components (w/w) useful for treating an eye disorder (e.g., dry eye syndrome) is as follows: brimonidine tartrate in the amount of 0.01% to 0.5% by weight, typically about 0.1 to 0.3% and loteprednol etabonate 0.01 to 0.2% by weight, typically about 0.04 to 0.06%, surfactant such as Polysorbate 80 at about 0.02%-2% by weight or poloxamer/tyloxapol at about 0.1% and 0.25% by weight; carbomer copolymer (type A or type B) about 0.05% by weight; tonicity agent (glycerine or includes glycerine about 2.2% by weight; sodium citrate and tris buffer of pH 6.0-8.0, sodium EDTA in the amount of about 0.02% or less by weight; an oil (e.g., castor oil) in the amount of about 1.25% by weight.

Another example of a topical ophthalmic combination formulation with its various components (w/w) useful for treating an eye disorder (e.g., dry eye syndrome) is as follows: brimonidine tartrate in the amount of 0.01% to 0.5% by weight, typically about 0.1 to 0.2% and loteprednol etabonate 0.01 to 0.3% by weight, typically about 0.15 to 0.2%, a surfactant such as Polysorbate 80 at about 0.02%-2% by weight, typically about 0.75 to 1.5%; a copolymer or combination of carbomers (type A or type B) about 0.05-0.1% by weight; tonicity agent (e.g., glycerin) about 2.2% by weight; buffer solution (e.g., sodium citrate and/or tris buffer) to adjust the final pH of 6.0-8.0, preferably pH 6.0-pH7.0; and an oil (e.g., castor oil) in the amount of about 1.25% by weight; acid or bases to adjust the pH.

Yet another example of a topical ophthalmic combination formulation with its various components (w/w) useful for treating an eye disorder (e.g., dry eye syndrome) is as follows: brimonidine tartrate in the amount of 0.01% to 0.5% by weight, preferably about 0.1% to 0.2% and loteprednol etabonate 0.01% to 0.5% by weight, preferably about 0.1% to 0.3%, Carbopol 971 at about 0.1% to 0.4% by weight, poloxamer/tyloxapol at about 0.1% and 0.3% by weight; tonicity agent (glycerin or includes glycerin about 1% to 3% by weight; sodium citrate and tris buffer of pH 6.0-8.0; sodium EDTA in the amount of about 0.02% or less by weight.

An example of a topical heterogeneous ophthalmic emulsion and or suspension with its various components (w/w) useful for treating an eye disorder (e.g., dry eye syndrome) is as follows: brimonidine tartrate in the amount of 0.05% to 0.2% by weight; loteprednol etabonate in the amount of 0.05% to 0.25% by weight; surfactant such as Polysorbate 80 at about 0.5%-1% by weight by weight; carbomer copolymer about 0.05% to 0.6% by weight; tonicity agent (e.g., glycerine) about 2.2% by weight; buffer solution (e.g., citrate and/or tris buffer) to maintain pH of about 6.0 to pH of about 8.0; an oil (e.g., castor oil) in the amount of about 1.25% by weight; the remaining being water. Alternatively, the oil can be a medium chain triglyceride in the range from 0.5-4%, typically at about 2% by weight. To prepare this formulation, all water-soluble components were added and heated (about 60-70° C.). A lipophilic solution was prepared using a lipophilic solvent (e.g., castor oil) and heated to about 60-70° C. Heterogeneous solution was formed by rapid addition of lipophilic solution into water phase followed by high shear mixing. Other excipients and APIs were mixed together to heterogenous emulsion or suspension solution. The sterilized heterogeneous solution can be filled into single dose disposable tubes by BFS technology or the like or into multi dose container/closure.

Still another example of a topical ophthalmic combination formulation with its various components (w/w) useful for treating an eye disorder (e.g., dry eye syndrome) is as follows: brimonidine tartrate in the amount of 0.01% to 0.5% by weight, preferably about 0.1 to 0.2% and loteprednol etabonate 0.01 to 0.5% by weight, preferably about 0.1 to 0.3%, povidone at about 0.6% by weight, poloxamer/tyloxapol at about 0.1% and 0.25% by weight; tonicity agent (glycerin or includes glycerin about 1 to 3% by weight; sodium citrate and tris buffer of pH 6.0-8.0; sodium EDTA in the amount of about 0.02% or less by weight.

Ophthalmic pharmaceutical compositions can also be formulated with the compositions shown in Table below. Heterogeneous solution formulation can be prepared according to the process described below where the water-insoluble active(s) are added to the oil phase (e.g., castor oil) before introducing the oil phase to the aqueous phase.

Ophthalmic pharmaceutical compositions can be formulated with the compositions shown in Table below. Heterogeneous solution formulations can be prepared according to the process described below where the water-insoluble active(s) are added after the formation of heterologous solution as the dispersion or suspension.

Exemplary Heterogeneous Solution Formulation Process Flow (Process I):
1. Oil phase: Mixed appropriate amounts of castor oil and polysorbate 80 until uniformity was obtained;
2. Aqueous phase: Mixed required amounts of Pemulen, water and glycerin until uniformity was obtained
3. Performed primary mixing of oil and aqueous phase mixtures from steps 1 and 2;
4. Performed high shear mixing and form heterogeneous solution from step 3;
5. Confirmed heterogeneous solution properties via in process testing The above steps of the process flow need not be carried out in the same order. Useful amount of each component is provided in the table below.

| Ingredient | Range per g | Other substitutes | Function |
| --- | --- | --- | --- |
| Brimonidine | 0.2 to 5 mg | | Active Pharmaceutical Ingredient* |
| Tartrate | 0.1 to 3 mg | | |
| Lifitegrast | 3 to 100 mg | | |
| Loteprednol etabonate | 0.1 to 20 mg | | |
| Castor Oil | 5-100 mg | Olive oil, Oleic acid | Oil Phase |
| Polysorbate 80 | 0.1 to 40 mg | Polysorbate-20, Poloxamer 188 | A component to both help facilitate the formation of the heterogeneous mixture and improve its stability. |
| Pemulen TR-2 | 0.1 to 2 mg | N/A | Emulsion Stabilizer |
| Glycerin | 0-100 mg | Trehalose, sorbitol, mannitol, xylitol | Tonicity-Adjusting Agent |
| Sodium Citrate Dihydrate | 0-20 mg | Phosphate, tris, histidine, acetate, succinate | Maintain pH |
| Tris Base | 0-15 mg | | Maintain pH |
| Preservative | Optional | benzalkonium chloride (BAK), stabilized oxychloro complex (Purite) | For multidose and non-sterile products |
| Base for pH | | pH 5 to 8 | Maintain pH |
| Acid for pH | | pH 5 to 8 | Maintain pH |
| Water for Injection | | | Vehicle |

*The emulsion formulation contains at least two active ingredients of which at least one active ingredient is water soluble. For example, formulations containing different combinations of active ingredients are: bromonidine or brimonidine tartrate + lifitegrast, or brimonidine or brimonidine tartrate and loteprednol or loteprednol etabonate.

Exemplary heterogeneous Solution Formulation Process Flow (Process II):
1. Oil phase: Mixed appropriate amounts of castor oil and polysorbate 80 until uniformity was obtained;
2. Aqueous phase: Mixed required amounts of Pemulen, water and glycerin until uniformity was obtained
3. Performed primary mixing of oil and aqueous phase mixtures from steps 1 and 2;
4. Performed high shear mixing and form heterogeneous solution from step 3;
5. Mixed other excipients and APIs.
6. Confirmed heterogeneous solution/emulsion/suspension properties via in process testing The above steps of the process flow (II) need not be carried out in the same order. Useful amount of each component is provided in the table below.

| Ingredient | Range per g | Other substitutes | Function |
| --- | --- | --- | --- |
| Brimonidine | 0.2 to 5 mg | | Active Pharmaceutical Ingredient* |
| Tartrate | 0.1 to 3 mg | | |
| Lifitegrast | 3 to 100 mg | | |
| Loteprednol etabonate | 0.1 to 20 mg | | |
| Castor Oil | 5-100 mg | Olive oil, Oleic acid | Oil Phase |
| Polysorbate 80 | 0.1 to 40 mg | Polysorbate-20, Poloxamer 188 | A component to both help facilitate the formation of the heterogeneous mixture and improve its stability. |
| Pemulen TR-2 | 0.1 to 2 mg | N/A | Emulsion Stabilizer |
| Carbopol 974P | 1 to 10 mg | Carbomers type A and B | Viscosity modifier |
| Glycerin | 0-100 mg | Trehalose, sorbitol, mannitol, xylitol | Tonicity-Adjusting Agent |
| Sodium Citrate Dihydrate | 0-20 mg | Phosphate, tris, histidine, acetate, succinate | Maintain pH |
| Tris Base | 0-15 mg | | Maintain pH |
| Preservative | Optional | benzalkonium chloride (BAK), stabilized oxychloro complex (Purite) | For multidose and non-sterile products |

-continued

| Ingredient | Range per g | Other substitutes | Function |
|---|---|---|---|
| Base for pH | | pH 5 to 8 | Maintain pH |
| Acid for pH | | pH 5 to 8 | Maintain pH |
| Water for Injection | | | Vehicle |

*The emulsion formulation contains at least two active ingredients of which at least one active ingredient is water soluble. For example, formulations containing different combinations of active ingredients are: bromonidine or brimonidine tartrate + liftegrast, or brimonidine or brimonidine tartrate and loteprednol or loteprednol etabonate.

Ophthalmic Suspension: Examples of combination product of brimonidine tartrate and loteprednol etabonate in an ophthalmic suspension formulation is provided below:

| Ingredient | Amount (mg)/g |
|---|---|
| Brimonidine Tartrate | 0.5-3 mg |
| Loteprednol Etabonate | 0.2-3 mg |
| Tyloxapol, USP | 1.5-4 mg |
| Poloxamer 188, NF | 0.5-2 mg |
| Carbopol 971 NF | 1.5-4 mg |
| Glycerin, USP | 15-30 mg |
| Sodium Citrate Dihydrate, USP | 1-2 mg |
| Sodium Hydroxide, USP | pH 6-7.5 |
| Water for Injection, USP | pH 6-7.5 |

| Ingredient | Amount (mg)/g |
|---|---|
| Brimonidine Tartrate | 0.5-3 mg |
| Loteprednol Etabonate | 0.2-3 mg |
| Tyloxapol, USP | 1.5-4 mg |
| Carbopol 971 NF | 1.5-4 mg |
| Glycerin, USP | 15-30 mg |
| Sodium Citrate Dihydrate, USP | 1-2 mg |
| Sodium Hydroxide, USP | pH 6-7.5 |
| Water for Injection, USP | pH 6-7.5 |

General process for producing aqueous formulation of the compositions of the invention is provided below. Briefly, for X Volume (V) of final formulation—complete following steps:

1(a). Mix Carboxymethycellulose-Na in X/4 V of water

1(b). Mix Polysorbate, API (Brimonidine Tartrate and liftegrast) and stabilizer (Trehalose/Mannitol) in X/2 V of water 2. Mix mixtures from 1(a) and 1(b) together until formation of homogenous or heterogeneous solution.

3. Add 10× Stock of buffer (X/10 V) to final mixture from Step 2.

4. Adjust osmomolarity by adding NaCl Stocks to mixture from Step 3.

5. Adjust pH by adding HCl/NaOH to mixture from Step 4.

6. Make final volume to V by adding water to mixture from Step 5.

7. Perform filter sterilization.

8. Filling (BFS).

Combined Aqueous Formulations:

Example of combination product of aqueous formulation of Brimonidine Tartrate and Liftegrast:

| Aqueous formulation | Range | Substitutes of Col. 1 |
|---|---|---|
| Carboxymethylcellulose-Na | 0.1 to 0.5% | Povidone, PEG 400, dextran, gelatin, hydroxy propyl methyl cellulose, vinyl polymers |
| Trehalose | 1 to 12% | Glycerol, sucrose, mannitol |
| Polysorbate-80 | 0.01 to 4% | Tyloxapol, pluronic F-68, poloxamer |
| Citrate, Tris | 1 mM to 100 mM | Phosphate, acetate, borate, histidine, succinate |
| Sodium Chloride | 0-140 mM | Magnesium chloride, calcium chloride, potassium chloride etc |
| NaOH/HCl as per requirement | N/A | N/A |
| pH | pH 5 to 8 | N/A |
| Osmolality | 200-400 mOsm | N/A |

The physical stability of these exemplary heterogeneous formulations can be monitored. For example, the heterogeneous solutions are allowed to stand for a period of time (e.g., 6 months) at 20 to 25° C., and the heterogeneity sizes are measured. The heterogeneity sizes within experimental error, should be identical at end of the test period to those measured right after the heterogeneous solution is prepared there by suggesting that there is no significant coalescence of the heterogeneity. Additionally, there should be no precipitation of the actives. Such results demonstrate that the heterogeneous formulations so prepared have superior physical stability.

Ophthalmic Gel Formulation:

Examples of combination product of brimonidine tartrate and loteprednol etabonate in an ophthalmic gel formulation:

| Ingredient | Amount (mg)/g |
|---|---|
| Brimonidine Tartrate | 0.5-3 mg |
| Loteprednol Etabonate | 0.2-3 mg |
| Tyloxapol, USP | 1.5-4 mg |
| Poloxamer 188, NF | 0.5-2 mg |
| Carbopol 980, NF | 2-6 mg |

-continued

| Ingredient | Amount (mg)/g |
|---|---|
| Glycerin, USP | 15-30 mg |
| Sodium Citrate Dihydrate, USP | 1-2 mg |
| Sodium Hydroxide, USP | pH 6-7.5 |
| Water for Injection, USP | pH 6-7.5 |

| Ingredient | Amount (mg)/g |
|---|---|
| Brimonidine Tartrate | 0.5-3 mg |
| Loteprednol Etabonate | 0.2-3 mg |
| Tyloxapol, USP | 1.5-4 mg |
| Poloxamer 188, NF | 0.5-2 mg |
| Polycarbophil | 2-6 mg |
| Glycerin, USP | 15-30 mg |
| Sodium Citrate Dihydrate, USP | 1-2 mg |
| Sodium Hydroxide, USP | pH 6-7.5 |
| Water for Injection, USP | pH 6-7.5 |

| Ingredient | Amount (mg)/g |
|---|---|
| Brimonidine Tartrate | 0.5-3 mg |
| Loteprednol Etabonate | 0.2-3 mg |
| Tyloxapol, USP | 1.5-4 mg |
| Poloxamer 188, NF | 0.5-2 mg |
| Carbopol 980, NF | 2-4 mg |
| Polycarbophil | 1-4 mg |
| Glycerin, USP | 15-30 mg |
| Sodium Citrate Dihydrate, USP | 1-2 mg |
| Sodium Hydroxide, USP | pH 6-7.5 |
| Water for Injection, USP | pH 6-7.5 |

| Ingredient | Amount (mg)/g |
|---|---|
| Brimonidine Tartrate | 0.5-3 mg |
| Loteprednol Etabonate | 0.2-3 mg |
| Tyloxapol, USP | 1.5-4 mg |
| Poloxamer 188, NF | 0.5-2 mg |
| Carboxymethylcellulose | 1-6 mg |
| Glycerin, USP | 15-30 mg |
| Sodium Citrate Dihydrate, USP | 1-2 mg |
| Sodium Hydroxide, USP | pH 6-7.5 |
| Water for Injection, USP | pH 6-7.5 |

Treatment Example:

Several drops of a given formulation exemplified herein were administered to the eye(s) of a patient suffering from dry eye syndrome. Reduction of the symptoms became noticeable within a reasonable period. The treatment was repeated one or more times daily while the condition persisted.

Combination Treatment Methods:

Mice were exposed to a desiccating environment combined with transdermal administration of scopolamine for a period of two weeks. Corneal surface inflammation and damage was assessed by scoring fluorescein staining. See FIG. 3A. Combination API formulation had the following composition (all units are based on 1 Kg of total composition): about 2-3 g of carbopols, about 20-25 g glycerin, about 0.1-1 g pemulen TR-2, about 10-15 g of castor oil, about 10 g of polysorbate 80, brimonidine tartrate and loteprednol etabonate in the amounts as described herein, suitable amount of sodium citrate and tris buffer, suitable amounts of sodium hydroxide and hydrochloric acid to adjust pH to a desired level along with a suitable amount of water as a carrier.

Results & Conclusions:

As shown in FIGS. 3A and 3B, combination API formulation having ingredients described above resulted in a statistically significant reduction of corneal fluorescein staining indicative of reduced corneal surface inflammation. The combination product was also compared against the two approved marketed products containing cyclosporine and lifitegrast. FIG. 3B. As can be seen, the combination product of the present invention afforded better result compared to the placebo, and two currently FDA approved drugs cyclosporine and lifitegrast.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All references including patents and publications cited herein are incorporated by reference in their entirety.

What is claimed is:

1. An ophthalmic composition comprising: an alpha 2 adrenergic agonist and cyclosporin.

2. The composition of claim 1, wherein said alpha 2 adrenergic agonist is selected from the group consisting of brimonidine, a pharmaceutically acceptable salt thereof, and a combination thereof.

3. The composition of claim 1 further comprising a pharmaceutically acceptable excipient.

4. The composition of claim 3, wherein said alpha 2 adrenergic agonist comprises from about 0.01% to about 0.5% w/w of the total composition.

5. The composition of claim 3, wherein said cyclosporin comprises from about 0.01% to about 0.5% w/w of the total composition.

6. The composition of claim 3, wherein said composition is formulated as a heterogeneous aqueous solution.

7. The composition of claim 6, wherein the heterogeneous aqueous solution is selected from the group consisting of an emulsion, a suspension, and a combination thereof.

8. The composition of claim 7, wherein said emulsion is a nanoemulsion.

9. The composition of claim 6, wherein the heterogeneous aqueous solution is selected from the group consisting of an emulsion, a gel, and combination thereof.

10. The composition of claim 3, wherein said composition is formulated as a homogeneous aqueous solution.

11. The composition of claim 3, wherein said pharmaceutically acceptable excipient comprises an emulsion stabilizing polymer, a water soluble polymer a surfactant, a tonicity modifier, a viscosity modifying agent, a stabilizer, or a combination thereof.

12. A method for treating an eye disorder selected from the group consisting of a dry eye syndrome, and an ocular surface and eyelid disorder, said method comprising administering to a subject in need of such a treatment a therapeutically effective amount of a composition of claim 1.

13. The method of claim 12, wherein said dry eye syndrome is selected from the group consisting of sjogren's syndrome, meibomian gland dysfunction and keratoconjunctivitis.

14. The method of claim 12, wherein said ocular surface and eyelid disorder comprises inflammation, pain and redness, and/or edema.

15. The method of claim 12, wherein said composition is administered topically to an eye of said subject.

* * * * *